United States Patent
Peña et al.

(10) Patent No.: US 7,166,574 B2
(45) Date of Patent: Jan. 23, 2007

(54) SYNTHETIC HEPARIN-BINDING GROWTH FACTOR ANALOGS

(75) Inventors: Louis A. Peña, Poquott, NY (US); Paul Zamora, Gaithersburg, MD (US); Xinhua Lin, Plainview, NY (US); John D. Glass, Shoreham, NY (US)

(73) Assignees: BioSurface Engineering Technologies, Inc., Rockville, MD (US); Brookhaven National Laboratory, Upton, NY (US)

( * ) Notice: Subject to any disclaimer, the term of this patent is extended or adjusted under 35 U.S.C. 154(b) by 464 days.

(21) Appl. No.: 10/224,268

(22) Filed: Aug. 20, 2002

(65) Prior Publication Data

US 2004/0038348 A1    Feb. 26, 2004

(51) Int. Cl.
*A61K 38/00*    (2006.01)
*A61K 38/19*    (2006.01)
*C07K 14/00*    (2006.01)

(52) U.S. Cl. .................. 514/12; 424/85.1; 530/397
(58) Field of Classification Search ............... 435/69.4, 435/69.6, 320.1, 325, 7.1, 7.2; 106/4; 530/399; 536/21; 514/56
See application file for complete search history.

(56) References Cited

U.S. PATENT DOCUMENTS

| | | |
|---|---|---|
| 5,563,046 A | 10/1996 | Mascarenhas et al. |
| 5,608,035 A | 3/1997 | Yanofsky et al. |
| 5,635,597 A | 6/1997 | Barrett et al. |
| 5,643,873 A | 7/1997 | Barrett et al. |
| 5,648,458 A | 7/1997 | Cwirla et al. |
| 5,654,276 A | 8/1997 | Barrett et al. |
| 5,668,110 A | 9/1997 | Barrett et al. |
| 5,674,977 A | 10/1997 | Gariepy |
| 5,679,637 A | 10/1997 | Lappi et al. |
| 5,684,136 A | 11/1997 | Godowski |
| 5,728,802 A | 3/1998 | Barrett et al. |
| 5,767,234 A | 6/1998 | Yanofsky et al. |
| 5,770,704 A | 6/1998 | Godowski |
| 5,773,569 A | 6/1998 | Wrighton et al. |
| 5,786,322 A | 7/1998 | Barrett et al. |
| 5,786,331 A | 7/1998 | Barrett et al. |
| 5,789,182 A | 8/1998 | Yayon et al. |
| 5,830,851 A | 11/1998 | Wrighton et al. |
| 5,861,476 A | 1/1999 | Barrett et al. |
| 5,866,113 A | 2/1999 | Hendriks et al. |
| 5,869,451 A | 2/1999 | Dower et al. |
| 5,880,096 A | 3/1999 | Barrett et al. |
| 5,902,799 A | 5/1999 | Herrmann et al. |
| 5,932,462 A | 8/1999 | Harris et al. |
| 5,952,474 A | 9/1999 | Kayman et al. |
| 5,955,588 A | 9/1999 | Tsang et al. |
| 5,965,532 A | 10/1999 | Bachovchin |
| 5,989,866 A | 11/1999 | Deisher et al. |
| 5,994,104 A | 11/1999 | Anderson et al. |
| 6,001,364 A | 12/1999 | Rose et al. ............... 424/193.1 |
| 6,011,002 A | 1/2000 | Pastan et al. |
| 6,030,812 A | 2/2000 | Bauer et al. |
| 6,051,648 A | 4/2000 | Rhee et al. |
| 6,121,236 A | 9/2000 | Ben-Sasson |
| 6,168,784 B1 | 1/2001 | Offord et al. ............... 424/85.1 |
| 6,174,530 B1 | 1/2001 | Rose et al. ............... 424/193.1 |
| 6,174,721 B1 | 1/2001 | Innis et al. |
| 6,214,795 B1 | 4/2001 | Benjamin et al. |
| 6,217,873 B1 | 4/2001 | Rose et al. ............... 424/193.1 |
| 6,235,716 B1 | 5/2001 | Ben-Sasson |
| 6,251,864 B1 | 6/2001 | Dower et al. |
| 6,284,503 B1 | 9/2001 | Caldwell et al. |
| 6,294,359 B1 | 9/2001 | Fiddes et al. |
| 6,323,323 B1 | 11/2001 | Sledziewski et al. |
| 6,326,468 B1 | 12/2001 | Canne et al. ............... 530/333 |
| 6,342,591 B1 | 1/2002 | Zamora et al. |
| 6,350,731 B1 | 2/2002 | Jehanli et al. |
| 6,377,349 B1 | 4/2002 | Fercher ............... 356/450 |
| 6,451,543 B1 | 9/2002 | Kochendoerfer et al. .... 435/7.1 |

FOREIGN PATENT DOCUMENTS

| | | |
|---|---|---|
| WO | WO 00/18921 | 4/2000 |
| WO | WO 02/04015 | 1/2002 |
| WO | WO 02/19963 | 3/2002 |
| WO | WO 02/20033 | 3/2002 |

OTHER PUBLICATIONS

Yoneda, et al, 2000, Nature Biotech., 18: 641-644.*
Verrecchio, et al, 2000, J. Biol. Chem., 275(11): 7701-7707.*
Pellegrini, L., 2001, Cuurent Opinion in Structural Biology, 11: 629-634.*
Arne Ostman, Maria Andersson, Ulf Hellman, and Carl-Henrik Heldin, "Identification of Three Amino Acids in the Platelet-derived Growth Factor (PDGF) B-chain that are Important for Binding to the PDGF B-Receptor" *The Journal of Biological Chemistry*, vol. 266, No. 16, Issue of Jun. 5, pp. 10073-10077, 1991.
David M. Brennand, Ulla Dennehy, Vincent Ellis, Michael F. Scully, Poonam Tripathi, Vijay V. Kakkar, Geeta Patel, Identification of a cyclic peptide inhibitor of platelet-derived growth factor-BB receptor-binding and mitogen-induced DNA synthesis in human fibroblasts, *FEBS Letters*, 413 (1997) 70-74.
Ahmed, Asif; Dunk, Caroline; Kniss, Douglas; Wilkes, Mark, "Role of VEFGF Receptor-1 (Fit-1) in Mediating Calcium-Dependent Nitric Oxide Release and Limiting DNA Synthesis in Human Trophoblast Cells," *Lab Invest*, vol. 76(6) Jun. 1997. 779-791.
Philip E. Dawson and Stephen B.H. Kent, "Synthesis of Native Proteins by Chemical Ligation," *Annu. Rev. Biochem*. 2000, 69:923-60.

(Continued)

*Primary Examiner*—Eileen O'Hara
*Assistant Examiner*—Sandra Wegert
(74) *Attorney, Agent, or Firm*—Stephen A. Slusher; Janeen Vilven; Peacock Myers, P.C.

(57) ABSTRACT

The invention provides synthetic heparin-binding growth factor analogs having at least one peptide chain that binds a heparin-binding growth factor receptor, covalently bound to a hydrophobic linker, which is in turn covalently bound to a non-signaling peptide that includes a heparin-binding domain. The synthetic heparin-binding growth factor analogs are useful as soluble biologics or as surface coatings for medical devices.

8 Claims, 11 Drawing Sheets

OTHER PUBLICATIONS

Roselyne Binetruy-Tournaire, Caroline Demangel, Bernard Malavaud, Roger Vassy, Sylvie Rouyre, Michael Kraemer, Jean Plouet, Claude Derbin, Gerard Perret and Jean Claude Mazie, "Identification of a peptide blocking vascular endothelial growth factor (VEGF)-mediated angiogenesis," *The EMBO Journal*, vol. 19 No. 7, pp. 1525-1533, 2000.

Khee Dong Eom, Zhenwei Miao, Jin-Long Yang, and James P. Tam, "Tandem Ligation of Multipartite Peptides with Cell-Permeable Activity," *J. Am. Chem. Soc.* 2003, 125, 73-83.

Gerd G. Kochendoerfer, Shiah-Yun Chen, Geng Mao, Sonya Cressman, Stacey Traviglia, Haiyan Shao, Christie L. Hunter, Donald W. Low, E. Neil Cagle, Maia Carnevali, Vincent Gueriguian, Peter J. Keoch, Heather Porter, Stephen M. Stratton, M. Con Wiedeke, Jill Wilken, Jie Tang, Jay J. Levy, Les P. Miranda, Milan M. Crnogorac, Suresh Kalbag, Paolo Botti, Janice Schindler-Horvat, Laura Savatski, John W. Adamson, Ada Kung, Stephen B.H. Kent, James A. Bradburne, "Design and Chemical Synthesis of Homogeneous Polymer-Modified Erythropoiesis Protein," *Science*, Feb. 7, 2003, vol. 299.

Ulla Engstrom, Ake Engstrom, Agneta Ernlund, Bengt Westermark, and Carl-Henrik Heldin, "Identification of a Peptide Antagonist for Platelet-derived Growth Factor," *The Journal of Biological Chemistry*, vol. 273, No. 25, Issue of Jun. 19, pp. 15811-15817, 1998.

David E. Hoke, Daniel Carson, and Magnus Hook, "A heparin binding synthetic peptide from human HIP/RPL29 fails to specifically differentiate between anticoagulantly active and inactive species of heparin," *Journal of Negative Results in BioMedicine* 2003, 2:1.

Gay, Cyril G. and Winkles, Jeffrey A.; Interleukin 1 regulates heparin-binding growth facto 2 gene expression in vascular smooth muscle cells; Proc. Natl. Acad. Sci. USA, vol. 88, pp. 296-300, Jan. 1991 Cell Biology.

Peter Carmeliet and Edward M. Conway, "Growing better blood vessels", *Nature Biotechnology* (2001) 19:1019-1020.

Thomas P. Richardson, Martin C. Peters, Alessandra B. Ennett, and David J. Mooney, "Polymeric system for dual growth factor delivery", *Nature Biotechnology* (2001) 19:1029-1034.

François Paris, Zvi Fuks, Anthony Kang, Paola Capodieci, Gloria Juan, Desiree Ehleiter, Adriana Haimovitz-Friedman, Carlos Cordon-Cardo, Richard Kolesnick, "Endothelial Apoptosis as the Primary Lesion Initiating Intestinal Radiation Damage in Mice", *Science* (2001) 293:293-297.

Luca Pellegrini, "Role of heparan sulfate in fibroblast growth factor signalling: a structural view". *Structural Biology* (2001) 11:629-634.

Takumi Takizawa, Makoto Yanagisawa, Wataru Ochiai, Kiyoshi Yasukawa, Takahiko Ishiguro, Kinichi Nakashima, Tetsuya Taga, "Directly Linked Soluble IL-6 Receptor-IL-6 Fusion Protein Induces Astrocyte Differentiation From Neuroepithelial Cells Via Activation Of STAT3", *Cytokine* (2001) 13:272-279.

Atsuko Yoneda, Masahiro Asada, Yuko Oda, Masashi Suzuki, and Toru Imamura, "Engineering of an FGF-proteoglycan fusion protein with heparin-independent, mitogenic activity", *Nature Biotechnology* (2000) 18:641-644.

Angela Verrecchio, Markus W. Germann, Barbara P. Schick, Brian Kung, Thomas Twardowski, and James D. San Antonio, "Design of Peptides with High Affinities for Heparin and Endothelial Cell Proteoglycans", *The Journal of Biological Chemistry* (2000) 275:7701-7707.

Marcus D. Ballinger, Venkatakrishna Shyamala, Louise D. Forrest, Maja Deuter-Reinhard, Laura V. Doyle, Jian-xin Wang, Lootsee Panganiban-Lustan, Jennifer R. Stratton, Gerald Apell, Jill A. Winter, Michael V. Doyle, Steven Rosenberg, and W. Michael Kavanaugh, "Semirational design of a potent, artificial agonist of fibroblast growth factor receptors", *Nature Biotechnology* (1999) 17:1199-1204.

Maemunah Hasan, Saloua Najjam, Myrtle Y. Gordon, Roslyn V. Gibbs, and Christopher C. Rider, "IL-12 is a Heparin-Binding Cytokine", *The Journal of Immunology* (1999) 162: 1064-1070.

R. Sood, A. Talwar-Trikha, SR Chakrabarti and G. Nucifora, "MDS1 EVI1 enhances TGF-$\beta$1 signaling and strengthens its growth-inhibitory effect. but the leukemia-associated fusion protein AML1 MDS1 EVI1, product of the t(3:21), abrogates growth-inhibition in response to TGF-$\beta$1", *Leukemia* (1999) 13:348-357.

José A. Andrades, Bo Han, José Becerra, Nino Sorgente, Frederick L. Hall, and Marcel E. Nimni, "A Recombinant Human TGF-$\beta$1 Fusion Protein with Collagen-Binding Domain Promotes Migration, Growth, and Differentiation of Bone Marrow Mesenchymal Cells", *Experimental Cell Research* (1999) 250:485-498.

Michael M. Dikov, Martha B. Reich, Lydia Dworkin, James W. Thomas, and Geraldine G. Miller, "A Functional Fibroblast Growth Factor-1 Immunoglobulin Fusion Protein", *The Journal of Biological Chemistry* (1998) 273: 15811-15817.

Marco Rusnati, Elena Tanghetti, Patrizia Dell'Era, Anna Gualandris, and Marco Presta, "$\alpha_v\beta_3$ Integrin Mediates the Cell-adhesive Capacity and Biological Activity of Basic Fibroblast Growth Factor (FGF-2) in Cultured Endothelial Cells", *Molecular Biology of the Cell* (1997) 8: 2449-2461.

Jasodhara Ray, Andrew Baird, and Fred H. Gage, "A 10-amino acid sequence of fibroblast growth factor 2 is sufficient for its mitogenic activity on neural progenitor cells", *Proc. Natl. Acad. Sci. USA* (1997) 94: 7047-7052.

* cited by examiner

Fig. 1

```
NH₂-K-K-Hex-Hex-Hex-RKRKLERIAR-amide
    | |  _____/ _____/
    N N    C18 spacer   Heparin
    R R                 Binding
    F F                 Domain
    H H
    S S
    W W
    D D
    C-C
    I I
    K K
    T T
    W W
    A A
    S S  } Receptor
    D D    Binding
    T Y    Domain
    F F
    V V
    L L
    V V
    C-C
    Y Y
    D D
    D D
    G G
    S S
    E E
    A A
    | |
   NH₂ NH₂
```

Fig. 2

NH₂-K-K-Hex-Hex-Hex-RKRKLERIAR-amide

Hex-Hex-Hex: C18 spacer

RKRKLERIAR: Heparin Binding Domain

Branches from the two K residues (Receptor Binding Domain):

```
Y Y
R R
S S
R R
K K
Y Y
S S
S S
W W
Y Y
V V
A A
L L
K K
R R
|  |
NH₂ NH₂
```

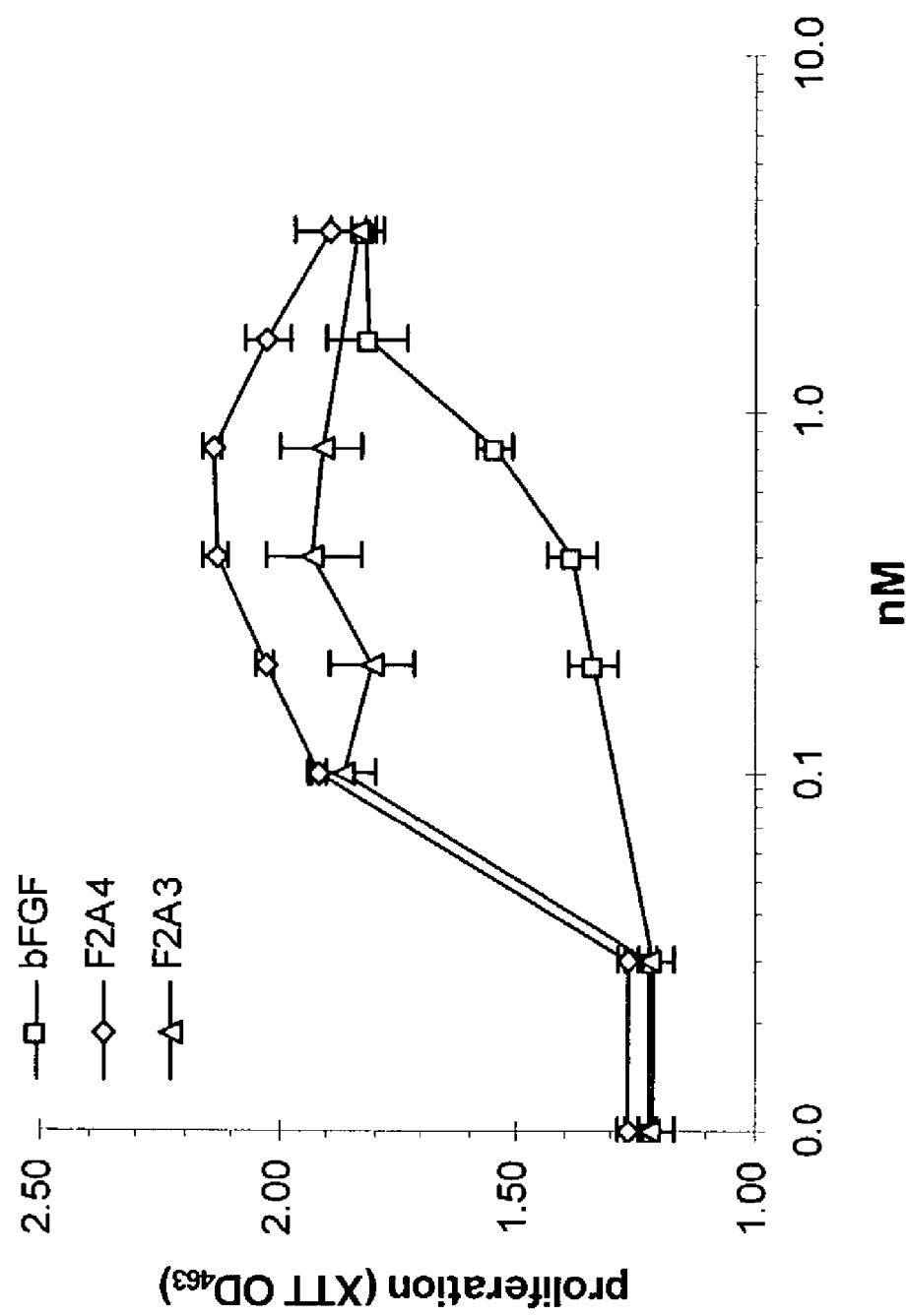

SYNTHETIC HEPARIN-BINDING GROWTH FACTOR ANALOGS

This invention was made with Government support under contract number DE-AC02-98CH10886, awarded by the U.S. Department of Energy. The Government has certain rights in the invention.

FIELD OF THE INVENTION

The invention relates to the field of synthetic peptides and analogs of heparin-binding growth factors, particularly analogs having a hydrophobic linker region and a heparin-binding region. The invention further relates to the clinical uses of such analogs as soluble drugs and also as coatings for medical devices.

BACKGROUND

The heparin-binding growth factors (HBGFs) constitute a large class of growth factors that includes the 23 fibroblast growth factors identified to date (FGFs 1–23), HBBM (Heparin-binding brain mitogen), HB-GAF (heparin-binding growth associated factor). HB-EGF (heparin-binding EGF-like factor) HB-GAM (heparin-binding growth associated molecule), TGF-α (transforming growth factor-α), TGF-βs (transforming growth factor-βs), PDGF (platelet-derived growth factor), EGF (epidermal growth factor). VEGF (vascular endothelial growth factor), IGF-1 (insulin-like growth factor-1), IGF-2 (insulin-like growth factor-2), HGF (hepatocyte growth factor), IL-1 (interleukin-1), IL-2 (interleukin-2), IFN-α (interferon-α), IFN-γ (interferon-y), TNF-α (tumor necrosis factor-α), SDGF (Schwannoma-derived growth factor) and the many other growth factors, cytokines, lymphokines and chemokines that have an affinity for heparin.

Peptides from natural HBGFs that bind heparin-binding growth factor receptors have been identified. See for example Ray et al., Proc. Natl. Acad. Sci. USA 94: 7047–7052 (1997). These authors demonstrated that two amino acid sequences from FGF-2 are sufficient to block the mitogenic activity of FGF-2 on neural progenitor cells. The first peptide is a ten amino acid sequence, from amino acids 65–74, the second peptide extends from amino acids 115–129.

In an alternative approach, an artificial peptide that binds a heparin-binding growth factor receptor was identified by a phage display method. Ballinger et al., Nature BioTechnology 17: 1199–1204 (1999) used this technique to isolate a 28 amino acid peptide called C19, binds FGF-2 receptors, but by itself fails to stimulate biological activity. The peptide has no amino acid sequence identity with any known FGF.

HBGFs useful in prevention or therapy of a wide range of diseases and disorders may be purified form natural sources or produced by recombinant DNA methods, however, such preparations are expensive and generally difficult to prepare.

Some efforts have been made to generate heparin-binding growth factor analogs. For example, natural PDGF occurs as an A chain and a B chain arranged in head-to-head (AA or BB) homodimers, or (AB or BA) heterodimers. Thus, U.S. Pat. No. 6,350,731 to Jehanli et al. discloses PDGF analogs in which two synthetic PDGF receptor-binding domains are covalently linked through a polyglycine or an N-(4-carboxy-cyclohexylmethyl)-maleimide (SMCC) chain to mimic the natural active polypeptide dimer.

U.S. Pat. No. 6,235,716 to Ben-Sasson discloses analogs of angiogenic factors. The analogs are branched multivalent ligands that include two or more angiogenic homology regions connected by a multilinker backbone.

U.S. Pat. No. 5,770,704 (the '704 patent) to Godowski discloses conjugates for activating receptor tyrosine kinases, cytokine receptors and members of the nerve growth factor receptor superfamily. The conjugates include at least two ligands capable of binding to the cognate receptor, so that the binding of the respective ligands induces oligomerization of these receptors. The ligands disclosed in the '704 patent are linked by covalent attachment to various nonproteinaceous polymers, particularly hydrophilic polymers, such as polyvinylalcohol and polyvinylpyrrolidone, and the polyvinylalkene ethers, including polyethylene glycol and polypropylene glycol. The ligands include hepatocyte growth factor (HGF) peptide variants that each bind HGF receptor, thereby causing receptor dimerization and activation of the biological activity of the HGF receptor dimer.

U.S. Pat. No. 6,284,503 (the '503 patent) to Caldwell et al. discloses a composition and method for regulating the adhesion of cells and biomolecules to hydrophobic surfaces and hydrophobic coated surfaces for cell adhesion, cell growth, cell sorting and biological assays. The composition is a biomolecule conjugated to a reactive end group activated polymer. The end group activated polymer includes a block copolymer surfactant backbone and an activation or reactive group. The block copolymer may be any surfactant having a hydrophobic region capable of adsorbing onto a hydrophobic surface, and a hydrophilic region which extends away from the surface when the hydrophobic region is adsorbed onto the hydrophobic surface. The '503 patent discloses that the biomolecules that may be conjugated to the end group activated polymer include natural or recombinant growth factors, such as PDGF, EGF, TGFo, TGFB, NGF, IGF-I, IGF-II, GH and GHRF, as well as multi-CSF (II-3), GM-CSF, G-CSF, and M-CSF.

Other workers have described compositions that include homologs and analogs of fibrobast growth factors (FGFs). See for example U.S. Pat. No. 5,679,673 to Lappi and Baird; U.S. Pat. No. 5,989,866 to Deisher et al. and U.S. Pat. No. 6,294,359 to Fiddes et al. These disclosures relate to FGF homologs or analogs that are either conjugated to a toxic moiety and are targeted to the FGF receptor-bearing cells; or are homologs or analogs that modulate the biological pathways through the signal transduced by the FGF receptor upon binding by the FGF homolog or analog.

The above described homologs, analogs, conjugates or ligands each include a receptor-binding domain. However, none of the disclosed compositions further include both a linker and a non-signaling peptide containing a heparin-binding domain. Moreover, none of these or other known heparin-binding growth factor analogs provide the advantages described herein below. There is still a need for new peptide analogs of HBGFs, particularly for those that function as agonists. In particular, there is still a need for cost-effective synthetic peptide agonists of heparin-binding growth factor receptors, particularly synthetic heparin-binding growth factor agonists useful for coating medical devices and as soluble biologics.

SUMMARY OF THE INVENTION

The present invention provides synthetic heparin-binding growth factor analogs that include a molecule having the formula (I):

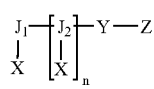

formula I

Each X in formula I represents a synthetic peptide chain that has a minimum of three amino acid residues, has a maximum of about fifty amino acid residues, and binds a heparin-binding growth factor receptor (HBGFR).

n is an integer equal to 0 or 1; $J_1$ represents an amino acid; and $J_2$ represents a diamino acid when n=1, or is absent when n=0.

Y represents a linker that is sufficiently hydrophobic to bind non-covalently to a polystyrene/polycaprolactone-like surface, and includes a chain of a minimum of about ten atoms and a maximum of about one hundred atoms. Y is not found in the natural ligand of the HBGFR, and is covalently bonded to $J_1$ and Z when n=0, or to $J_2$ and Z when n=1.

Z represents a non-signaling peptide that comprises a heparin binding domain, encompassing an amino acid sequence that includes (i) a minimum of one heparin binding motif, (ii) a maximum of ten heparin binding motifs, and (iii) a maximum of thirty amino acids. When n=1 the synthetic peptide chains, the two X domains are identical. The peptide analog of formula I has an avidity for heparin such that the synthetic heparin-binding growth factor analog binds heparin in 0.48M NaCl, but is eluted by 1M NaCl.

The present invention further provides other synthetic fibroblast growth factor (FGF) analogs that include a molecule having the formula (II):

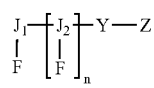

formula II

In this synthetic fibroblast growth factor analog each F represents a synthetic peptide chain that binds a fibroblast growth factor receptor (FGFR) and has a minimum of three amino acid residues and a maximum of about fifty amino acid residues.

n is 0 or 1; $J_1$ represents an amino acid; $J_2$ represents a diamino acid when n=1, or is absent when n=0; Y represents a linker that comprises a chain of a minimum of about ten and a maximum of about one hundred atoms, and is not found in the natural ligand of the fibroblast growth factor receptor, and is covalently bonded to $J_1$ and Z when n=0, or to $J_2$ and Z when n=1.

Z represents a non-signaling peptide that comprises a heparin binding domain, comprising an amino acid sequence that comprises (i) a minimum of one heparin binding motif, a maximum of ten heparin binding motifs, and (iii) a maximum of thirty amino acids. When n=1 the synthetic peptide chains, F are identical. The synthetic heparin-binding growth factor analog has an avidity for heparin such that the synthetic heparin-binding growth factor analog binds heparin in 0.48M NaCl, but is eluted by 1M NaCl.

The present invention yet further provides a method for treating a mammal that has been exposed to a harmful dose of radiation, the method comprising administering to the mammal an effective dose of a synthetic heparin-binding growth factor analog of formula II. The method includes administering to the mammal an effective dose of the synthetic heparin-binding growth factor analog to ameliorate the harmful effects of the radiation, which may include mucositis, G.I. syndrome, or radionecrosis.

The present invention also provides a method for delivering an active peptide to a mammal, particularly a human. The method includes providing a medical device coated on the surface thereof via non-covalent bonds with a synthetic heparin-binding growth factor analog of formula I or formula II and placing the medical device onto a surface of, or implanting the medical device into, the mammal.

BRIEF DESCRIPTION OF THE FIGURES

FIG. 1: Sequence of synthetic peptide analog F2A3.
FIG. 2: Sequence of synthetic peptide analog F2A4.
FIG. 6: Stimulation of cell proliferation in fibroblast cultures. Mitogenic dose response of F2A3 and F2A4 versus bFGF.

DETAILED DESCRIPTION OF THE INVENTION

Figure 3:
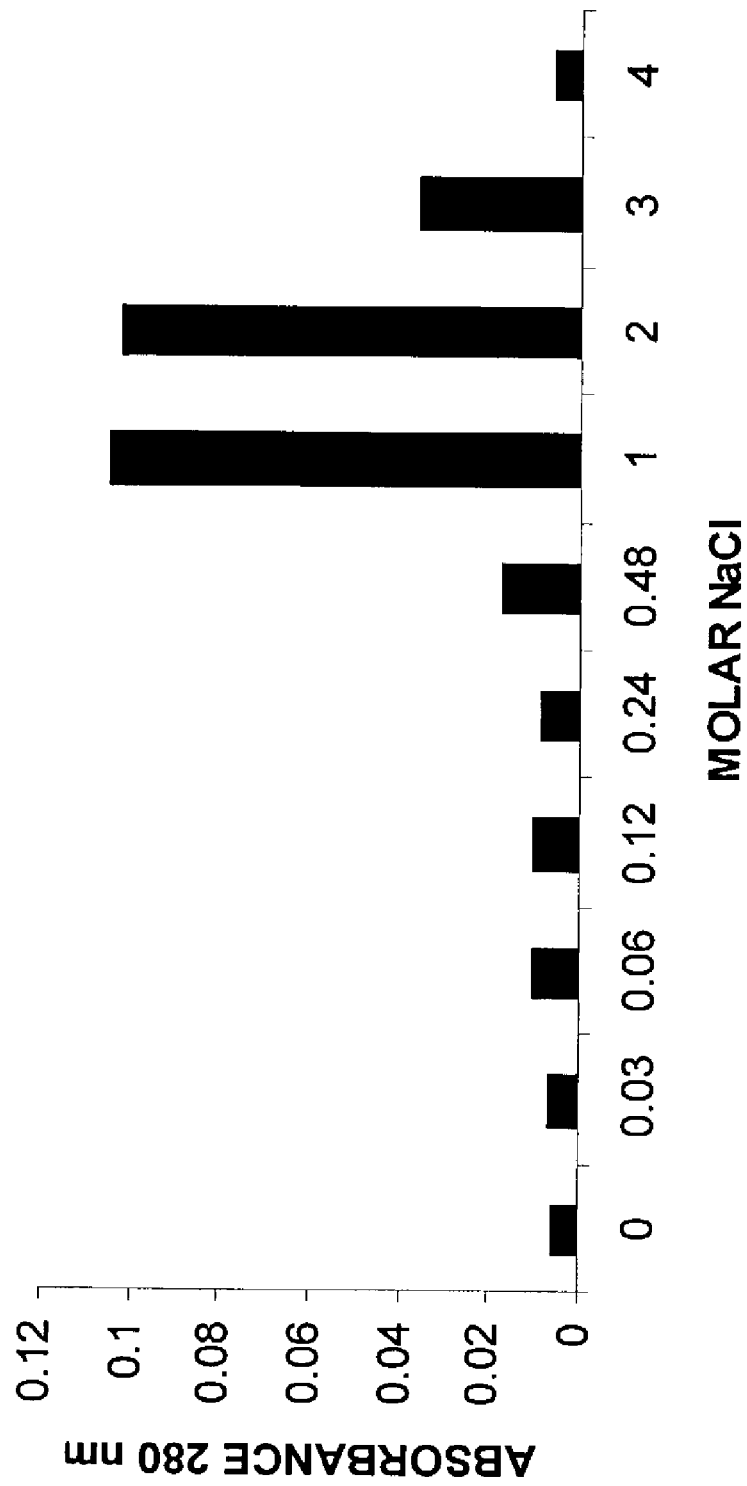
FIG. 3: Elution of F2A3 from a heparin affinity column.

Each synthetic heparin-binding growth factor analog of the invention is an analog of a particular heparin-binding growth factor (HBGF) that binds to one or more of the receptors bound by the particular HBGF. The synthetic HBGF analog may be an analog of a hormone, a cytokine, a lymphokine, a chemokine or an interleukin.

In one aspect the synthetic heparin-binding growth factor analog of the present invention is a molecule of formula I, or a molecule of formula II (shown above). HBGFs include any growth factor that binds selectively to heparin. For example, the HBGF can be any of the known FGFs (FGF-1 to FGF-23), HBBM (Heparin-binding brain mitogen), HB-GAF (heparin-binding growth associated factor), HB-EGF (heparin-binding EGF-like factor) HB-GAM (heparin-binding growth associated molecule, also known as plelotrophin, PTN, HARP), TGF-α (transforming growth factor-α), TGF-βs (transforming growth factor-βs), VEGF (vascular endothelial growth factor), EGF (epidermal growth factor), IGF-1 (insulin-like growth factor-1), IGF-2 (insulin-like growth factor-2), PDGF (platelet derived growth factor), RANTES, SDF-1, secreted frizzled-related protein-1 (SFRP-1), small inducible cytokine A3 (SCYA3), inducible cytokine subfamily A member 20(SCYA20), inducible cytokine subfamily B member 14 (SCYB 14), inducible cytokine subfamily D member 1 (SCYD1), stromal cell-derived factor-1 (SDF-1), thrombospondins 1, 2, 3 and 4 (THBS1–4), platelet factor 4 (PF4), lens epithelium-derived growth factor (LEDGF), midikine (MK), macrophage inflammatory protein (MIP-1), moesin (MSN), hepatocyte growth factor (HGF, also called SF), placental growth factor, IL-1 (interleukin-1), IL-2 (interleukin-2), IL-3 (interleukin-3), IL-6 (interleukin-6), IL-7 (interleukin-7), IL-10 (interleukin-10), IL-12 (interleukin-12), IFN-α (interferon-α), IFN-γ (interferon-γ), TNF-α (tumor necrosis factor-α ), SDGF (Schwannoma-derived growth factor), nerve growth factor, neurite growth-promoting factor 2 (NEGF2), neurotrophin, BMP-2 (bone morphogenic protein 2), OP-1 (osteogenic protein 1, also called BMP-7), keratinocyte growth factor (KGF), interferon-y inducible protein-20, RANTES, and HIV-tat-transactivating factor, amphiregulin (AREG), angio-associated migratory cell protein (AAMP), angiostatin, betacellulin (BTC), connective tissue growth factor (CTGF), cysteine-rich angiogenic inducer 61 (CYCR61), endostatin, fractalkine/neuroactin, or glial derived neurotrophic factor (GDNF), GRO2, hepatoma-derived growth factor (HDGF), granulocyte-macrophage colony stimulating factor (GMCSF), and the many growth factors, cytokines, interleukins and chemokines that have an affinity for heparin.

The amino acid sequences of many of these and other HBGFs are available from the National Library of Medicine Protein Database at the world wide web address of ncbi.nlm.nih.gov/entrez. These HBGF amino acid sequences on the foregoing internet site are hereby incorporated by reference. The use of synthetic HBGF analogs incorporating the amino acid sequences of the receptor binding domains from these and other HBGFs is specifically contemplated in the present invention.

In particular embodiments of the present invention, the synthetic HBGF analog of the present invention consists essentially of the molecule of formula I or of formula II, i.e. the molecule of formula I or formula II is the major active component in the synthetic HBGF analog composition.

In other particular embodiments, the synthetic HBGF analog of the present invention consists entirely of the molecule of formula I or of formula II, i.e. the molecule of formula I or formula II is the only component in the synthetic HBGF analog composition.

The Heparin-binding Growth Factors of Formula I

The regions X, Y and Z of the synthetic HBGF analogs of formula I or formula II include amino acid residues. An amino acid residue is defined as —NHRCO—, where R can be hydrogen or any organic group. The amino acids can be D-amino acids or L-amino acids. Additionally, the amino acids can be σ-amino acids, β-amino acids, γ-amino acids, or δ-amino acids and so on, depending on the length of the carbon chain of the amino acid.

The amino acids of the X, Y and Z component regions of the synthetic HBGF analogs of the invention can include any of the twenty amino acids found naturally in proteins, i.e. alanine (ala, A), arginine (Arg, R), asparagine (Asn, N), aspartic acid (Asp, D), cysteine (Cys, C), glutamic acid (Glu, E), glutamine (Gln, Q), glycine (Gly, G), histidine (His, H), isoleucine, (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V).

Furthermore, the amino acids of the X, Y and Z component regions of the synthetic HBGF analogs of the invention can include any of the naturally occurring amino acids not found naturally in proteins, e.g. β-alanine, betaine (N,N,N-trimethylglycine), homoserine, homocysteine, γ-amino butyric acid, ornithine, and citrulline.

Additionally, the amino acids of the X, Y and Z component regions of the synthetic HBGF analogs of the invention can include any of the non-biological amino acids, i.e. those not normally found in living systems, such as for instance, a straight chain amino-carboxylic acid not found in nature. Examples of straight chain amino-carboxylic acids not found in nature include 6-aminohexanoic acid, and 7-aminoheptanoic acid, 9-aminononanoic acid and the like.

In formula I when n is 0, the molecule of the present invention includes a single X region and the molecule is a linear chain. When n is 1 in formula I, the molecule includes two X regions that are identical in amino acid sequence. In the latter case the molecule is a branched chain that may also be constrained by cross-links between the two X regions as described below. In this embodiment, each HBGF analog of the present invention can bind two HBGFRs and induce receptor dimerization. Advantageously, the dimerization in turn potentiates enhanced receptor signaling activity of the HBGFRs.

When n is 0 in formula I, the X region of the synthetic HBGF analog of the invention is covalently linked through an amino acid, $J_1$ to the hydrophobic region Y.

When n is 1 in formula I, one X region is covalently linked through an amino acid $J_1$, which is in turn covalently linked to a second amino acid, $J_2$, which is a diamino acid. $J_1$ is linked to one amino group of the diamino acid, $J_2$. The second X region is covalently linked to $J_2$ through the second amino group of the diamino acid. $J_2$ is then covalently linked through its carboxy terminus to the Y region of the synthetic HBGF analog.

The amino acid $J_1$ of formula I can be any of the amino acids described above. The diamino acid $J_2$ of formula I can be any diamino acid, such as for instance lysine, or ornithine, or any other amino acid having two amino groups.

The region, X of formula I of the synthetic HBGF analogs of the present invention is a synthetic peptide chain that binds an HBGFR. Region X can, for example, have any amino acid sequence that binds an HBGFR, and can include amino acid sequences that are identical to a portion of the amino acid sequence of a HBGF. Alternatively, X can have an amino acid sequence homologous rather than identical to the amino acid sequence of an HBGF. The particular HBGFR bound by the synthetic HBGF analog of the invention may or may not be the cognate receptor of the original HBGF, i.e. the synthetic HBGF analog may additionally or solely bind to the receptor of a different HBGF.

The term 'homologous', as used herein refers to peptides that differ in amino acid sequence at one or more amino acid positions when the sequences are aligned. For example, the amino acid sequences of two homologous peptides can differ only by one amino acid residue within the aligned amino acid sequences of five to ten amino acids. Alternatively, two homologous peptides of ten to fifteen amino acids can differ by no more than two amino acid residues when aligned. In another alternative, two homologous peptides of fifteen to twenty or more amino acids can differ by up to three amino acid residues when aligned. For longer peptides, homologous peptides can differ by up to approximately 5%, 10%, 20% or 25% of the amino acid residues when the amino acid sequences of the two peptide homologs are aligned.

Particularly useful amino acid sequences as X regions of formula I include homologs of fragments of naturally occurring HBGFs that differ from the amino acid sequences of natural growth factor in only one or two or a very few positions. Such sequences preferably include conservative changes, where the original amino acid is replaced with an amino acid of a similar character according to well known principles; for example, the replacement of a non-polar amino acid such as alanine with valine, leucine, isoleucine or proline; or the substitution of one acidic or basic amino acid with another of the same acidic or basic character.

In another alternative, the X region of the synthetic HBGF analog can include an amino acid sequence that shows no detectable homology to the amino acid sequence of any HBGF. Peptides or growth factor analogs useful as components of the X region of the synthetic analogs of the present invention, that have little or no amino acid sequence homology with the cognate growth factor and yet bind HBGFRs may be obtained by any of a wide range of methods, including for instance, selection by phage display. See as an example: Sidhu et al. Phage display for selection of novel binding peptides. Methods Enzymol 2000; vol. 328:333–63. An example of such a peptide that binds an HBGFR yet has no homology to any known HBGF is the C19 peptide sequence described below in Example 1.

The X region of the synthetic HBGF analogs of the invention can have any length that includes an amino acid sequence that effectively binds an HBGFR. Preferably, the synthetic HBGF analogs have a minimum length of at least approximately three amino acid residues. More preferably, the synthetic HBGF analogs have a minimum length of at least approximately six amino acid residues. Most preferably the synthetic HBGF analogs have a minimum length of at least approximately ten amino acid residues. The synthetic HBGF analogs of the invention preferably, also have a maximum length of up to approximately fifty amino acid residues. More preferably, the synthetic HBGF analogs have a maximum length of up to approximately forty amino acid residues. Most preferably the synthetic HBGF analogs have a maximum length of up to approximately thirty amino acid residues.

In one embodiment of the synthetic HBGF analogs that include two X regions, the X regions are covalently cross linked. Suitable cross links can be formed by S—S bridges of cysteines linking the two X regions. Alternatively, the cross link can be conveniently formed during simultaneous and parallel peptide synthesis of the X region amino acids chains by incorporating a lanthionine (thio-dialanine) residue to link the two identical X chains at alanine residues that are covalently bonded together by a thioether bond. In another method the two X region amino acid chains can be cross-linked by introducing a cross-linking agent, such as a dicarboxylic acid, e.g. suberic acid (octanedioic acid), or the like, thereby introducing a hydrocarbon bridge between the two identical X regions having a free amino, hydroxyl or thiol group.

In the synthetic HBGF analogs of the present invention, the Y region of formula I represents a linker that is sufficiently hydrophobic to non-covalently bind the HBGF analog to a polystyrene or polycaprolactone surface, or the like. In addition, the Y region may bind to other hydrophobic surfaces, particularly the hydrophobic surfaces formed from materials used in medical devices. Such surfaces are typically hydrophobic surfaces. Examples of suitable surfaces include but are not limited to those formed from hydrophobic polymers such as polycarbonate, polyester, polypropylene, polyethylene, polystyrene, polytetrafluoroethylene, expanded polytetrafluoroethylene, polyvinyl chloride, polyamide, polyacrylate, polyurethane, polyvinyl alcohol, polyurethane, poly ethyl vinyl acetate, poly(butyl methacrylate), poly(ethylene-co-vinyl acetate), polycaprolactone, polylactide, polyglycolide and copolymers of any two or more of the foregoing; siloxanes such as 2,4,6,8-tetramethylcyclotetrasiloxane; natural and artificial rubbers; glass; and metals including stainless steel, titanium, platinum, and nitinol. Preferably, the binding of the HBGF analogs to the hydrophobic surface is of sufficient quantity to be detected by an analytical method such as an enzyme-linked immunoassay or a biological assay.

The Y region of formula I includes a chain of atoms or a combination of atoms that form a chain. Typically, the chains are chains of carbon atoms, that may also optionally include oxygen, nitrogen or sulfur atoms, such as for example chains of atoms formed from amino acids (e.g. amino acids found in proteins, as listed above; naturally occurring amino acids not found in proteins, such as ornithine and citrulline; or non natural amino acids, such as amino hexanoic acid; or a combination of any of the foregoing amino acids).

The chain of atoms of the Y region of formula I is covalently attached to $J_1$ or $J_2$, and to peptide Z. The covalent bonds can be, for example, amide or ester bonds.

Preferably, the Y region includes a chain of a minimum of about nine atoms. More preferably, the Y region includes a chain of a minimum of about twelve atoms. Most preferably, the Y region includes a chain of a minimum of about fifteen atoms. For example, the Y region may be formed from a chain of at least four, at least five or at least six amino acids. Alternatively, the Y region may be formed from a chain of at least one, at least two, or at least three aminohexanoic acid residues.

Preferably, the Y region includes a chain of a maximum of about fifty atoms. More preferably, the Y region includes a chain of a maximum of about forty-five atoms. Most preferably, the Y region includes a chain of a maximum of about thirty-five atoms. For Example, the Y region may be formed from a chain of up to about twelve, up to about fifteen, or up to about seventeen amino acids.

The amino acid sequence of the Y region of formula I is an artificial sequence, i.e. it does not include any amino acid sequence of four or more amino acid residues found in a natural ligand of a HBGF.

In a particular embodiment, the Y region includes a hydrophobic amino acid residue, or a chain of hydrophobic amino acid residues. The Y region can, for example, include one or more aminohexanoic acid residues, such as one, two, three or more aminohexanoic acid residues.

In another particular embodiment, the Y region of the molecule of formula I can include a branched or unbranched, saturated or unsaturated alkyl chain of between one and about twenty carbon atoms. In a further embodiment, the Y region can include a chain of hydrophobic residues, such as for instance, ethylene glycol residues. For instance, the Y region can include at least about three, or at least about four, or at least about five ethylene glycol residues. Alternatively, the Y region can include up to about twelve, up to about fifteen, or up to about seventeen ethylene glycol residues.

In another alternative embodiment, the Y region can include a combination of amino acid and hydrophobic residues.

The hydrophobic Y region of the HBGF of formula I of the present invention is covalently linked to the Z region.

The Z region of the molecule of formula I is a heparin-binding region and can include one or more heparin-binding motifs, BBxB or BBBxxB as described by Verrecchio et al. J. Biol. Chem. 275: 7701, (2000). Alternatively, the Z region can include both BBxB and BBBxxB motifs (where B represents lysine, arginine, or histidine, and x represents a naturally occurring, or a non-naturally occurring amino acid). For example, the heparin-binding motifs may be represented by the sequence [KR][KR][KR]X(2)[KR], (SEQ ID NO:1) designating the first three amino acids as each independently selected from lysine or arginine, followed by any two amino acids and a sixth amino acid which is lysine or arginine.

The number of heparin binding motifs is not critical. For instance, the Z region may include at least one, at least two, at least three or at least five heparin-binding motifs. Alternatively, the Z region may include up to a maximum of about ten heparin-binding motifs. In another alternative embodiment, the Z region includes at least four, at least six or at least eight amino acid residues. Further, the Z region may include up to about twenty, up to about, twenty-five, or up to about thirty amino acid residues.

In a preferred embodiment, the amino acid sequence of the Z region is RKRKLERIAR (SEQ ID No:2). Heparin-binding domains that bear little or no sequence homology to known heparin-binding domains are also contemplated in the present invention. As used herein the term "heparin-binding" means binding to the $-NHSO_3^-$ and sulfate modified polysaccharide, heparin and also binding to the related modified polysaccharide, heparan.

The Z region of the synthetic HBGF analogs of the present invention confers the property of binding to heparin in low salt concentrations, up to about 0.48M NaCl, forming a complex between heparin and the Z region of the factor analog. The complex can be dissociated in 1M NaCl to release the synthetic HBGF analog from the heparin complex.

The Z region is a non-signaling peptide. Accordingly, when used alone the Z region binds to heparin which can be bound to a receptor of a HBGF, but the binding of the Z region peptide alone does not initiate or block signaling by the receptor.

The C-terminus of the Z region may be blocked or free. For example, the C terminus of the Z region may be the free carboxyl group of the terminal amino acid, or alternatively, the C terminus of the Z region may be a blocked carboxyl group, such as for instance, an amide group. In a preferred embodiment the C terminus of the Z region is an amidated arginine as shown in FIGS. 1 and 2.

The Heparin-binding Growth Factors of Formula II

In another particular aspect, the synthetic peptide analog of the present invention is a molecule of formula II. The synthetic FGF analog represented by formula II (shown above) is an analog of an FGF which can be any FGF, such as any of the known FGFs, including all 23 FGFs from FGF-1 to FGF-23.

The X region of the molecule of formula II can include an amino acid sequence found in an FGF, such as for instance, FGF-2 or FGF-7. Alternatively, the X region can include a sequence not found in the natural ligand of the FGFR bound by the molecule of formula II.

The F and Z regions of formula II are subject to the same limitations in size and sequence as described above for the corresponding X and Z regions of formula I.

The Y region of the HBGF analogs of formula II have the same size limitations as the Y region of the HBGF analogs of formula I. However, the overall physical characteristics of the Y region of formula II is not limited to hydrophobic properties and can be more varied. For example, the Y region of formula II can be polar, basic, acidic, hydrophilic or hydrophobic. Thus, the amino acid residues of the Y region of formula II can include any amino acid, or polar, ionic, hydrophobic or hydrophilic group.

The X region of the synthetic HBGF of formula II can include an amino acid sequence that is 100% identical to the amino acid sequence found in a fibroblast growth factor or an amino acid sequence homologous to the amino acid sequence of a fibroblast growth factor. For instance, the X region can include an amino acid sequence that is at least about 50%, at least about 75%, or at least about 90% homologous to an amino acid sequence from a fibroblast growth factor. The fibroblast growth factor can be any fibroblast growth factor, including any of the known or yet to be identified fibroblast growth factors.

In a particular embodiment, the synthetic FGF analog of the invention is an agonist of the HBGFR. When bound to the HBGFR, the synthetic HBGF analog initiates a signal by the HBGFR.

In a further particular embodiment, the synthetic FGF analog of the invention is an antagonist of the HBGFR. When bound to the HBGFR, the synthetic HBGF analog blocks signaling by the HBGFR.

In another particular embodiment of the present invention, the synthetic FGF analog is an analog of FGF-2 (also known as basic FGF, or bFGF). In another particular embodiment of the present invention, the binding of the synthetic FGF analog to an FGF receptor initiates a signal by the FGF receptor. In a further particular embodiment, the binding of the synthetic FGF analog to the FGF receptor blocks signaling by the FGF receptor.

In a yet further particular embodiment, the present invention provides a synthetic FGF analog of FGF-2, wherein the FGF receptor-binding domain is coupled through a hydrophobic linker to a heparin-binding domain. In another particular embodiment, the present invention provides a synthetic FGF analog of FGF-2, wherein the amino acid sequence of the F region is YRSRKYSSWYVALKR (SEQ ID No:3) from FGF-2. In yet another particular embodiment, the present invention provides a synthetic FGF analog wherein the amino acid sequence of the F region is (SEQ ID No:4), NRFHSWDCIKTWASDTFVLVCYDDGSEA.

Methods of Synthesizing the Heparin-binding Growth Factor Analogs

The synthesis of the analogs of the invention can be achieved by any of a variety of chemical methods well known in the art. Such methods include bench scale solid phase synthesis and automated peptide synthesis in any one of the many commercially available peptide synthesizers. Preferably, the synthesizer has a per cycle coupling efficiency of greater than 99 percent.

The analogs of the present invention can be produced by stepwise synthesis or by synthesis of a series of fragments that can be coupled by similar well known techniques. See for instance Nyfeler, Peptide synthesis via fragment condensation. Methods Mol Biol 1994;35:303–16; and Merrifield, Concept and early development of solid-phase peptide synthesis. Methods in Enzymol 1997; 289:3–13. These methods are routinely used for the preparation of individual peptides.

Advantageously, in the case where the analogs of formula I or of formula II of the invention include two identical X region amino acid sequences, the synthesis of these identical X region peptides may be performed in parallel. By this method each cycle of addition adds an amino acid to both of the X region peptides, greatly facilitating the synthesis of these branched molecules.

Peptide libraries that can be used to screen for a desired property, such as binding to an HBGFR can be prepared by adaptations of these methods. See for instance, Fox, Multiple peptide synthesis, Mol Biotechnol 1995, 3(3):249–58; and Wade and Tregear, Solid phase peptide synthesis: recent advances and applications. Austral Biotechnol 1993, 3(6): 332–6.

In a particular embodiment, the synthetic HBGF analog of the invention is an agonist of the HBGFR. When bound to the HBGFR, the synthetic HBGF analog initiates a signal by the HBGFR.

In another particular embodiment, the synthetic HBGF analog of the invention is an antagonist of the HBGFR. When bound to the HBGFR, the synthetic HBGF analog blocks signaling by the HBGFR.

In a particular aspect, the invention provides a method for stimulating growth factor receptor signaling in a cell by contacting the cell with an effective amount of a synthetic HBGF analog according to formula I. The effective amount can be readily determined by one of skill in the art. The signaling can be signaling that results in cytokine release from the cell, stimulation or inhibition of proliferation or differentiation of the cell, chemotaxis of the cell, stimulation or inhibition of the immune system of the mammal.

Methods of Use of the HBGFs of the Invention

The HBGF analogs of the invention provide a cost effective and potentially unlimited source of biologically active molecules that are useful in a number of ways, including as soluble prophylactic or therapeutic pharmaceutical agents, such as for instance for administration as a soluble drug for prevention or treatment of various diseases, including for example, uses in cancer therapy and radioprotection.

The synthetic HBGF analogs of present invention are also useful as biologically active agents for coating of medical devices, such as for instance, sutures, implants and medical instruments to promote biological responses, for instance, to stimulate growth and proliferation of cells, or healing of wounds.

In one aspect, the present invention provides a method for treating a mammal that has been exposed to a harmful dose of radiation. The method includes administering an effective dose of a synthetic HBGF analog of the invention which is an FGF analog to the mammal. The treatment is particularly useful in the prevention or treatment of mucositis, gastrointestinal syndrome (G.I. syndrome), or radionecrosis such as can result from exposure to radiation. The HBGF analog can be administered parenterally, orally, or topically. Alternatively, the HBGF analog can be delivered locoregionally, e.g. on an analog coated medical device.

In a particular embodiment of the method, the above-described method, the mammal is a human. In another particular embodiment of the method, the HBGF analog is an FGF-2 analog or an FGF-7 analog.

The term "medical device" as used herein means a device that has one or more surfaces in contact with an organ, tissue, blood or other bodily fluid in an organism, preferably a mammal, particularly, a human. Medical devices include, for example, extracorporeal devices for use in surgery such as blood oxygenators, blood pumps, blood sensors, tubing used to carry blood, and the like which contact blood that is returned to the patient. The term can also include endoprostheses implanted in blood contact in a human or animal body, such as vascular grafts, stents, pacemaker leads, heart valves, and the like that are implanted in blood vessels or in the heart. The term can further include devices for temporary intravascular use such as catheters, guide wires, and the like that are placed in blood vessels or the heart for purposes of monitoring or repair. The term can further include nerve electrodes, muscle electrodes, implantable pulse generators, implantable drug pumps, and defibrillators. Moreover, the term medical device can include sutures, graft materials, wound coverings, nerve guides, bone wax, aneurysm coils, embolization particles, microbeads, dental implants, bone prostheses, tissue scaffolds, artificial joints or a controlled release drug delivery devices.

The surface of the medical device can be formed from any of the commonly used materials suitable for use in medical devices, such as for instance, stainless steel, titanium, platinum, tungsten, ceramics, polyurethane, polytetrafluoroethylene, extended polytetrafluoroethylene, polycarbonate, polyester, polypropylene, polyethylene, polystyrene, polyvinyl chloride, polyamide, polyacrylate, polyurethane, polyvinyl alcohol, polycaprolactone, polylactide, polyglycolide, polysiloxanes (such as 2,4,6,8-tetramethylcyclotetrasiloxane), natural rubbers, or artificial rubbers, or block polymers or copolymers thereof.

Methods for coating biological molecules onto the surfaces of medical devices are known. See for instance U.S. Pat. No. 5,866,113 to Hendriks et al., the specification of which is hereby incorporated by reference. Tsang et al. in U.S. Pat. No. 5,955,588 teach a non-thrombogenic coating composition and methods for using the same on medical devices, and is incorporated herein by reference. Zamora et al in U.S. Pat. No. 6,342,591 teach an amphipathic coating for medical devices for modulating cellular adhesion composition, and is incorporated herein by reference.

Other coating inventions that teach away from the current invention include the following: Ottersbach et al in U.S. Pat. No. 6,248,811 teach a bioactive coating that covalently fixes coatings on the surfaces of substrates, and therefore teaches away from the current invention. Ragheb et al in U.S. Pat. No. 6,299,604 describes a coating layer posited on one surface of the structure wherein a bioactive material is posited on at least a portion of the coating layer and diffuses out through a porous layer. Similarly, Chudzik et al. in U.S. Pat. No. 6,344,035 describe a bioactive agent release coating that includes a bioactive agent in combination with a mixture of a polymer component. Sprague in U.S. Pat. No. 6,140,127 describe a method of coating an intravascular stent with an endothelial cell adhesive five amino acid peptide. This coating is preferably carried out by activating the intravascular stent using plasma glow discharge, applying an additional layer(s), applying a tresylation solution containing pyridine and tresyl chloride, and applying a five amino acid peptide having the sequence glycine-arginine-glutamic acid-aspartic acid-valine to result in chemical conjugation of the peptide to the surface. Steber et al. in U.S. Pat. No. 5,801,141 teach an implant for the parenteral administration of an essentially uniform and continuous amount of a biologically active protein, a peptide or a polypeptide which comprises a compacted, indented and partially coated composition containing from one to three layers of a homogeneous core mixture comprising about 20% to about 80% of the growth factor, the biologically active fragment or the derivative; about 10% to about 75% of a fat, a wax or a mixture thereof; 0% to about 25% of a buffer, a salt, a sugar or a mixture thereof; and 0% to about 15% of a filler, on a weight basis of the total weight of the core mixture.

In one embodiment the invention provides a method for delivering an active peptide to a mammal, the method includes (i) providing a medical device coated on its surface with a synthetic HBGF analog of formula I or of formula II, the synthetic HBGF analog being bound to the surface of the medical device by non-covalent bonds; and (ii) placing the medical device onto a surface of, or implanting the medical device into, the mammal.

In a particular embodiment of the above method, the non-covalent bonds are associations between the heparin binding domain of the synthetic HBGF analog and a heparin-containing compound bound to the surface of the medical device. The heparin-containing compound bound to the surface of the medical device can be any heparin-containing compound, such as for instance, benzyl-bis(dimethylsilylmethyl)oxy carbamoyl-heparin.

In another particular embodiment of the above method, the medical device is not pre-coated with a heparin-containing compound before being coated with the synthetic HBGF analog of formula I or of formula II.

Heparin-binding Growth Factors

The fibroblast growth factors, FGFs constitute a family of related proteins controlling normal growth and differentiation of mesenchymal, epithelial, and neuroectodermal cell types. Homologs have been found in a wide variety of species. FGFs show a very high affinity to heparin and are therefore also referred to as heparin-binding growth factors (HBGFs). As used herein, the term HBGFs includes all FGFs.

Two main types of FGF are known. The first type of FGF was isolated initially from brain tissue. It was identified by its proliferation-enhancing activities for murine fibroblasts, such as 3T3 cells. Due to its basic pI the factor was named basic FGF (bFGF, or HBGF-2, heparin-binding growth factor-2) and is now generally referred to as FGF-2. This is the prototype of the FGF family.

Another type of FGF, also initially isolated from brain tissues, is acidic FGF (aFGF, also known as HBGF-1, heparin-binding growth factor-1 or HBGF-α, heparin-binding growth factor-α), now generally referred to as FGF-1. It was identified by its proliferation-enhancing activity for myoblasts.

Other fibroblast growth factors belonging to the same family include FGF-3 (or HBGF-3, heparin-binding growth factor-3, originally called int-2; see Fekete, Trends in Neurosci. 23(8): 332, 2000), FGF-4 (HBGF-4, heparin-binding growth factor-4, initially recognized as the product of the oncogene hst; see Sakamoto et al., Proc. Natl. Acad. Sci. USA 91(26):12368–72), and FGF-5 (originally called HBGF-5, see Bates et al. Biosynthesis of human fibroblast growth factor 5. Mol Cell Biol 11: 1840–1845 (1991); Burgess and Maciag, The heparin-binding (fibroblast) growth factor family of proteins. Ann. Rev. Biochem. 58: 575–606 (1989); and Zhan et al. The human FGF-5 oncogene encodes a novel protein related to fibroblast growth factors. Mol Cell Biol 8: 3487–3495, 1988)

FGF-6 (HBGF-6, sometimes called hst-2 or oncogene hst-1 related growth factor, see Iida et al. Human hst-2 (FGF-6) oncogene: cDNA cloning and characterization. Oncogene 7: 303–9 (1992); and Marics et al. Characterization of the HST-related FGF-6 gene, a new member of the fibroblast growth factor gene family. Oncogene 4: 335–40, (1989).

FGF-7 or K-FGF is also known as KGF, keratinocyte growth factor, (See Aaronson et al. Keratinocyte growth factor. A fibroblast growth factor family member with unusual target cell specificity. Annals NY Acad Sci 638: 62–77 (1991); Finch et al. Human KGF is FGF-related with properties of a paracrine effector of epithelial cell growth. Science 245: 752–5 (1989); Marchese et al. Human keratinocyte growth factor activity on proliferation and differentiation of human keratinocytes: differentiation response distinguishes KGF from EGF family. J. Cellular Physiol 144: 326–32, 1990).

FGF-8 was found to be identical to androgen-induced growth factor, AIGF and has been well studied (See Blunt et al. Overlapping expression and redundant activation of mesenchymal fibroblast growth factor (FGF) receptors by alternatively spliced FGF-8 ligands. J. Biol Chem 272(6): 3733–8 (1997); Dubrulle et al. FGF signaling controls somite boundary position and regulates segmentation clock control of spatiotemporal Hox gene activation. Cell 106: 219–232 (2001); Gemel et al. Structure and sequence of human FGF8. Genomics 35: 253–257 (1996); Tanaka et al. A novel isoform of human fibroblast growth factor 8 is induced by androgens and associated with progression of esophageal carcinoma. Dig. Dis. Sci. 46(5): 1016–21 (2001).

FGF-9 was originally called glia activating factor, or HBGF-9: See Miyamoto et al. Molecular cloning of a novel cytokine cDNA encoding the ninth member of the fibroblast growth factor family, which has a unique secretion pattern. Mol Cell Biol 13: 4251–9 (1993); Naruo et al. Novel secretory heparin-binding factors from human glioma cells (glia-activating factors) involved in glial cell growth. J. Biol. Chem 268: 2857–64 (1993).

FGF-10 is also called KGF-2, keratinocyte growth factor-2 (see Kok et al. Cloning and characterization of a cDNA encoding a novel fibroblast growth factor preferentially expressed in human heart. Biochem. Biophys. Res. Comm.255(3): 717–721, 1999).

Several FGF-related factors have been described as fibroblast growth factor homologous factors (FHFs) and are also referred to as FGF-11 (FHF-3), FGF-12 (FHF-1), FGF-13 (FHF-2, see Greene et al. Identification and characterization of a novel member of the fibroblast growth factor family. Eur J Neurosci 10(5): 1911–1925, 1998), and FGF-14 (FHF-4).

FGF-15 is expressed in the developing nervous system and was identified as a gene regulated by transcription factor E2A-Pbx1. McWhirter et al. A novel fibroblast growth factor gene expressed in the developing nervous system is a downstream target of the chimeric homeodomain oncoprotein E2A-Pbx1. Development 124(17): 3221–3232 (1997).

FGF-16 was isolated as a cDNA clone from rat heart by homology-based polymerase chain reaction expressing an FGF of 207 amino acids. FGF-16 is 73% identical to FGF-9. Miyake et al. Structure and expression of a novel member, FGF-16, of the fibroblast growth factor family. Biochem Biophys Res Commun 243(1): 148–152 (1998).

The cDNA encoding FGF-17 was isolated from rat embryos and encodes a protein of 216 amino acids. When expressed in 3T3 fibroblasts, mouse FGF-17 is transforming. During embryogenesis, FGF-17 is expressed at specific sites in forebrain, the midbrain-hindbrain junction, the developing skeleton and in developing arteries. See Hoshikawa et al. Structure and expression of a novel fibroblast growth factor, FGF-17, preferentially expressed in the embryonic brain. Biochem Biophys Res Commun 244(1): 187–191 (1998); and Xu et al. Genomic structure, mapping, activity and expression of fibroblast growth factor 17. Mechanisms of Development 83: 165–178 (1999).

The cDNA encoding FGF-18 was isolated from rat embryos encoding a protein of 207 amino acids. FGF-18 is a glycosylated protein and is most similar to FGF-8 and FGF-17. Injection of recombinant murine FGF-18 has been shown to induce proliferation in tissues of both epithelial and mesenchymal origin, particularly in liver and small intestine. Recombinant rat FGF-18 induces neurite outgrowth in PC12 cells. Recombinant murine FGF-18 protein stimulates proliferation in NIH 3T3 fibroblasts in vitro in a heparan sulfate-dependent manner. For general information see Hu et al. FGF-18, a novel member of the fibroblast growth factor family, stimulates hepatic and intestinal proliferation. Mol Cell Biol 18(10): 6063–6074 (1998); and Ohbayashi et al. Structure and expression of the mRNA encoding a novel fibroblast growth factor, FGF-18. J. Biol Chem 273(29): 18161–18164 (1998).

FGF-19 is related distantly to other members of the FGF family. FGF-19 mRNA is expressed in several tissues including fetal cartilage, skin, and retina, as well as adult gall bladder. It is overexpressed in a colon adenocarcinoma cell line. FGF-19 is a high affinity, heparin-dependent ligand for the FGF-4 receptor. See Xie et al. FGF-19, a novel fibroblast growth factor with unique specificity for FGFR4 Cytokine 11(10): 729–735 (1999).

FGF-20 is expressed in normal brain, particularly the cerebellum, and in some cancer cell lines. FGF-20 mRNA is expressed preferentially in the substantia nigra pars compacta. Recombinant FGF-20 protein induces DNA synthesis in a variety of cell types and is recognized by multiple FGF receptors. FGF-20 functions like an oncogene, causing a transformed phenotype when expressed in the 3T3 fibroblast cell line. These transformed cells are tumorigenic in nude mice. See Jeffers et al. Identification of a novel human fibroblast growth factor and characterization of its role in oncogenesis. Cancer Res 61(7): 3131–8 (2001); and Ohmachi et al. FGF-20, a novel neurotrophic factor, preferentially expressed in the substantia nigra pars compacta of rat brain. Biochem Biophys Res Commun 277(2): 355–60 (2000).

FGF-21 was isolated from mouse embryos. FGF-21 mRNA is most abundant in the liver with lower levels in the thymus. FGF-21 is most similar to human FGF-19. See Nishimura et al. Identification of a novel FGF, FGF-21, preferentially expressed in the liver. Biochim Biophys Acta 1492(1): 203–6 (2000).

The cDNA encoding FGF-22 (170 amino acids) was isolated from human placenta. FGF-22 is most similar to FGF-10 and FGF-7. Murine FGF-22 mRNA is expressed preferentially in the skin. FGF-22 mRNA in the skin is found preferentially in the inner root sheath of the hair follicle. See Nakatake et al. Identification of a novel fibroblast growth factor, FGF-22, preferentially expressed in the inner root sheath of the hair follicle. Biochim Biophys Acta 1517(3): 460–3 (2001).

FGF-23 is most similar to FGF-21 and FGF-19. The human FGF-23 gene maps to chromosome 12p13 linked to human FGF-6 gene. FGF-23 mRNA is expressed mainly in the brain (preferentially in the ventrolateral thalamic nucleus) and thymus at low levels. Missense mutations in the FGF-23 gene have been found in patients with autosomal dominant hypophosphataemic rickets. Overproduction of FGF23 causes tumor-induced osteomalacia, a paraneoplastic disease characterized by hypophosphatemia caused by renal phosphate wasting. See Yamashita et al. Identification of a novel fibroblast growth factor, FGF-23, preferentially expressed in the ventrolateral thalamic nucleus of the brain. Biochem Biophys Res Commun. 277(2): 494–8 (2000); and Shimada et al. Cloning and characterization of FGF23 as a causative factor of tumor-induced osteomalacia. Proc Natl Acad Sci (USA), 98(11): 6500–5 (2001).

HBBM (Heparin-binding brain mitogen) was isolated initially as a heparin binding protein from brain tissues of several species and is identical to heparin-binding neurite promoting factor. See Huber et al. Amino-terminal sequences of a novel heparin-binding protein with mitogenic activity for endothelial cells from human bovine, rat, and chick brain: high interspecies homology. Neurochem. Res 15: 435–439 (1990).

HB-GAF (heparin-binding growth associated factor) is a neurotrophic and mitogenic factor identical to HBNF (heparin-binding neurite-promoting factor). See Kuo et al. Characterization of heparin-binding growth-associated factor receptor in NIH 3T3 cells. Biochem Biophys Res Commun 182: 188–194 (1992).

HB-EGF (heparin-binding EGF-like factor) is found in conditioned media of cell line U937 and is also synthesized by macrophages and human vascular smooth muscle cells. HB-EGF is a monomeric heparin-binding O-glycosylated protein of 86 amino acids and is processed from a precursor of 208 amino acids. Several truncated forms of HB-EGF have been described. HB-EGF is a potent mitogen for NIH 3T3 cells, keratinocytes and smooth muscle cells, but not for endothelial cells. The mitogenic activity on smooth muscle cells is much stronger than for EGF and appears to involve interactions with cell surface heparan sulfate proteoglycans. HB-EGF is a major growth factor component of wound fluid and may play an important role in wound healing. See Abraham et al. Heparin-binding EGF-like growth factor: characterization of rat and mouse cDNA clones, protein domain conservation across species, and transcript expression in tissues. Biochem Biophys Res Commun 190: 125–133 (1993); and Higashiyama et al. A heparin-binding growth factor secreted by macrophage like cells that is related to EGF. Science 251: 936–9 (1991). Marikovsky et al. Appearance of heparin-binding EGF-like growth factor in wound fluid as a response to injury. Proc Natl Acad Sci (USA) 90: 3889–93.

HB-GAM (heparin-binding growth associated molecule) also referred to as HBNF (heparin-binding neurite promoting factor) is a protein of 15.3 kDa isolated as a heparin binding protein from brain tissues of several species. HB-GAM promotes growth of SW-13 cells in soft agar. Courty et al. Mitogenic properties of a new endothelial cell growth factor related to pleiotrophin. Biochem. Biophys. Res. Commun. 180: 145–151 (1991); and Hampton et al. Structural and functional characterization of full-length heparin-binding growth associated molecule. Mol. Biol. Cell. 3: 85–93 (1992).

TGF-beta (TGF-β) exists in at least five isoforms, known TGFβ1, TGFβ2, TGFβ3, TGF-β4 and TGF-β5 that are not related to TGF-α. Their amino acid sequences display homologies on the order of 70–80 percent. TGF-β1 is the prevalent form and is found almost ubiquitously while the other isoforms are expressed in a more limited spectrum of cells and tissues.

TGF-beta is the prototype of a family of proteins known as the TGF-beta superfamily. This family includes inhibins, Activin A, MIS (Mullerian activating substance) and BMPs (Bone morphogenic proteins). Burt, Evolutionary grouping of the transforming growth factor-beta superfamily. Biochem. Biophys. Res. Commun. 184: 590–5 (1992).

EXAMPLES

Example 1

The synthetic HBGF analog, F2A3, the structure of which is shown in FIG. 1, was synthesized by standard solid phase peptide synthesis methods. F2A3 has a structure according to formula II, in which the amino acid sequence of the F region, NRFHSWDCIKTWASDTFVLVCYDDGSEA (SEQ ID NO:4), corresponds to the C19 peptide sequence identified by Ballinger et al. (Nature Biotechnology 17:1199, 1999). The C19 peptides are covalently linked by peptide bonds through lysine residues, corresponding to $J_1$ and $J_2$, to one terminus of a tripeptide formed from three aminohexanoic acid residues corresponding to linker Y, and providing a hydrophobic space of 18 alkyl carbon atoms. The opposite terminus of the aminohexanoic acid tripeptide is covalently bound to heparin-binding peptide RKRKLERAIR (SEQ ID NO:2) corresponding to region Z.

The peptides were assembled stepwise by solid-phase synthesis on a substituted benzhydrylamine resin, using Fmoc chemistry for temporary protection of amino groups in the repetitive cycles. Branching of the chain was accomplished by stepwise growth of identical chains from the side-chain amino groups of consecutive lysyl residues. The completed peptide chains were cleaved from the resin as C-terminal amides by acidolysis, which also removed the acid-labile side-chain protecting groups.

The crude peptide preparation was first purified by heparin affinity chromatography. The crude preparation was solubilized in 10 mM HEPES (pH 7.0), loaded onto a HiTrap® Heparin HP column (Amersham Pharmacia Biotech, Piscataway, N.J., USA), and washed with 10 column volumes of 10 mM HEPES (pH 7.0). The peptide was then eluted with 2 M NaCl in 10 mM HEPES (pH 7.0), monitored by 280 nm absorbance. Peptide fractions were desalted and concentrated by loading onto Sep-Pak® C18 cartridges (Waters, Milford, Mass., USA), washed with 10 column volumes of water, and then eluted with 80% acetonitrile. Eluted fractions were lyophilized, redissolved in water, and the concentration was determined by BCA® Protein Assay Kit (Pierce Endogen, Rockford, Ill., USA) using bovine serum albumin as a reference.

Example 2

The synthetic HBGF analog, F2A4, as shown in FIG. 2, was synthesized by standard solid phase peptide synthesis methods. The amino acid sequences of F2A4 corresponding to regions Y and Z of formula II are identical to those of F2A3 described in Example 1. The amino acid sequence YRSRKYSSWYVALKR (SEQ ID NO:3), of the two F region peptides correspond to amino acids 115–129 of FGF-2 identified by Ray et al. (Proc. Natl. Acad. Sci. USA 94:7047–7052, 1997).

The crude preparation was purified as described above in Example 1.

Example 3

FIG. 3 shows the elution profile of F2A3 from a heparin affinity column. Mini columns were prepared with 0.5 ml heparin-agarose and washed extensively with water. F2A3 was loaded onto the column and rinsed with water. F2A3 was eluted from the column by stepwise increasing concentrations of NaCl as shown.

Example 4

Figure 4:
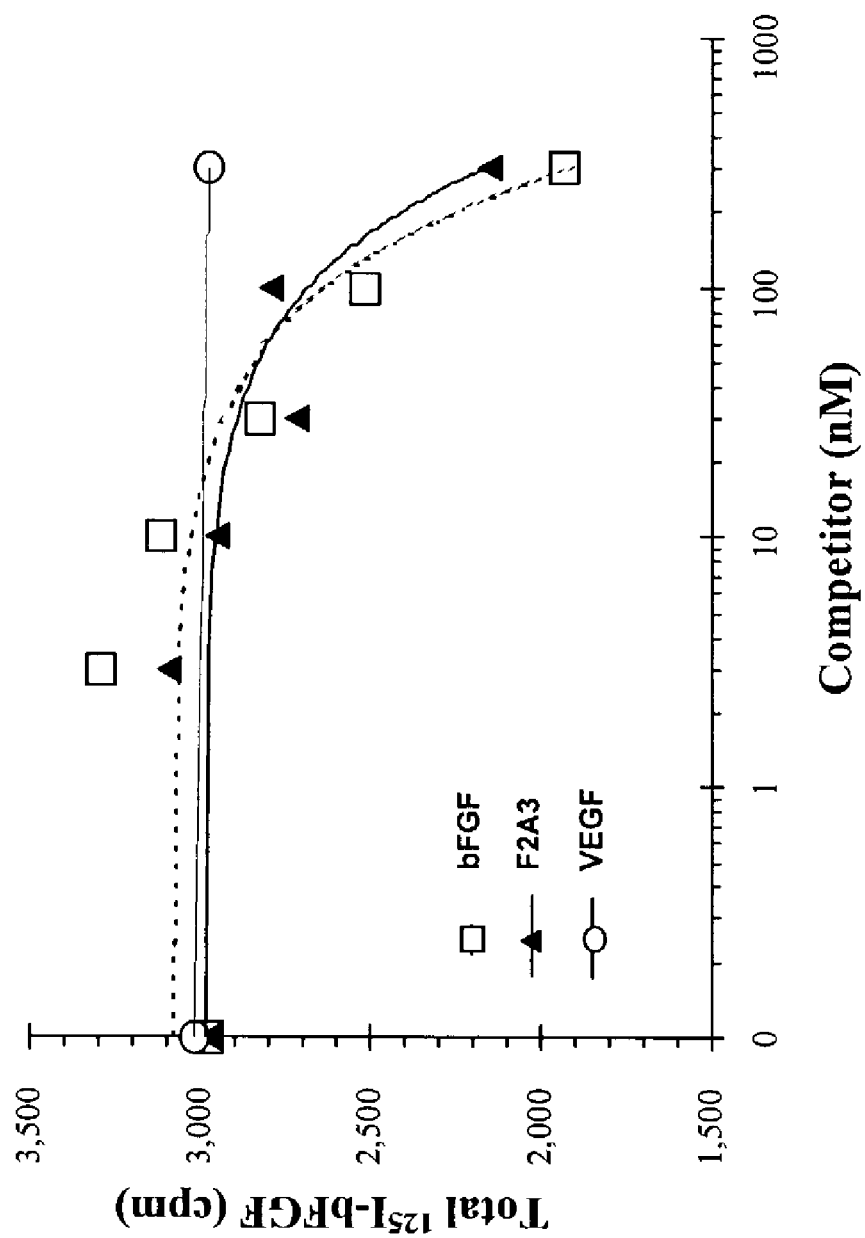
FIG. 4: Specific binding of F2A3 to FGFRs on HUVECs.

FIG. 4 shows the specific binding of F2A3 and F2A4 to HUVECs (Human umbilical vein endothelial cells). $^{125}$I-bFGF was incubated with intact HUVECs in the presence of unlabeled ligands at the indicated concentrations. The bound $^{125}$I-bFGF fraction at 4° C. was recovered from solubilized HUVEC membranes after stringent washing and quantitated in a gamma counter. F2A3 and F2A4 displaced $^{125}$I-bFGF (FGF-2) bound to FGF receptors of the HUVECs, while the unrelated heparin-binding cytokine, VEGF did not.

Example 5

Figure 5:
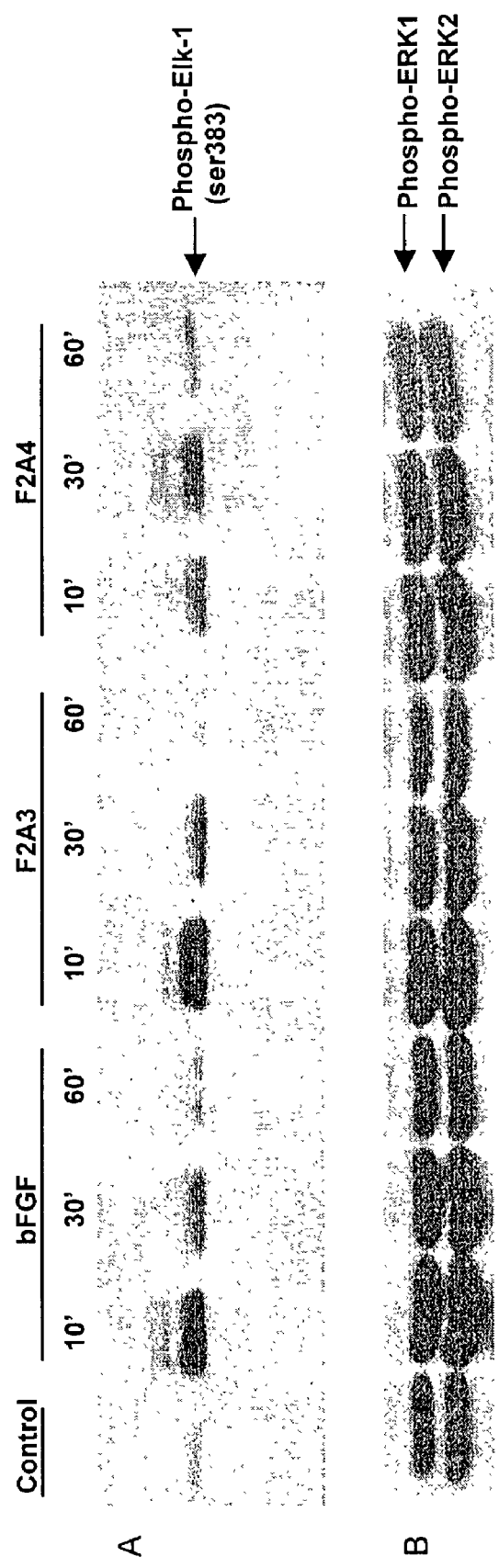
FIG. 5: Equivalence of bFGF analogs F2A3 and F2A4 to native, recombinant bFGF in MAP kinase phosphorylation and activation.

FIG. 5 shows the equivalence of bFGF analogs F2A3 and F2A4 to native, recombinant bFGF in MAP kinase phosphorylation and activation. C3H10T1/2 cells were stimulated with 3 nM of bFGF, F2A3 or F2A4 for 10, 30 or 60 minutes and lysed. (A) Active MAP kinase from cell lysates were immunoprecipitated with monoclonal anti-phosphop-44/42 MAP kinase (Thr202 and Tyr204). The resulting immunoprecipitate was incubated with an Elk-1 fusion protein in the presence of ATP. Phosphorylated Elk-1 at Ser 383 was visualized by western blotting using a phosphor-Elk-1 (Ser 383) antibody. (B) To reveal the phosphorylation of MAP kinase, cell lysates were analyzed by western blotting using monoclonal anti-phosphop-44/42 MAP kinase (Thr202 and Tyr204) antibody. The results show that both F2A3 and F2A4 activate Elk-1, as does bFGF, as shown by the phosphorylated Ser383 residue present in these samples at 10 mins. and absent from the untreated control. The level of phosphorylated Ser383 decreased successively from 10 mins. to 30 mins and even further at 60 mins. By contrast, the level of phosphor-ERK-1 and phosphor-ERK-2 was consistently high in the F2A3, F2A4 and bFGF treated samples at 10 mins., 30 mins and 60 mins, whereas the control untreated sample exhibited a distinguishably lower level of each of phosphor-ERK-1 and phosphor-ERK-2. These observations show that the HBGF analogs, F2A3 and F2A4 are biologically active as bFGF analogs in these assays.

Example 6

FIG. 6 shows the results of an assay for mitogenesis by F2A3 and F2A4 as compared with bFGF (FGF-2). C3H10T1/2 cells were grown in DMEM medium supplemented with 10% FBS (fetal bovine serum). Two days before the assay, cell culture medium was replaced with low serum medium (DMEM with 0.1% FBS ). At the start of the assay, cells were trypsinized and a single-cell suspension was seeded onto 96-well culture plates at 1,000 cells/well. Synthetic cytokine analog peptide or recombinant human FGF-2 were added to triplicate wells (100 μl/well final volume), and culture plates were returned to a 37° C. incubator. After three days, cell proliferation was quantified by the XTT Cell Proliferation Kit II (Roche Applied Science, Indianapolis, Ind., USA) according to manufacturer's instructions.

The analogs F2A3 and F2A4 provide higher specific activites at lower concentrations than bFGF as shown by the results of this assay.

Example 7

Figure 7A:
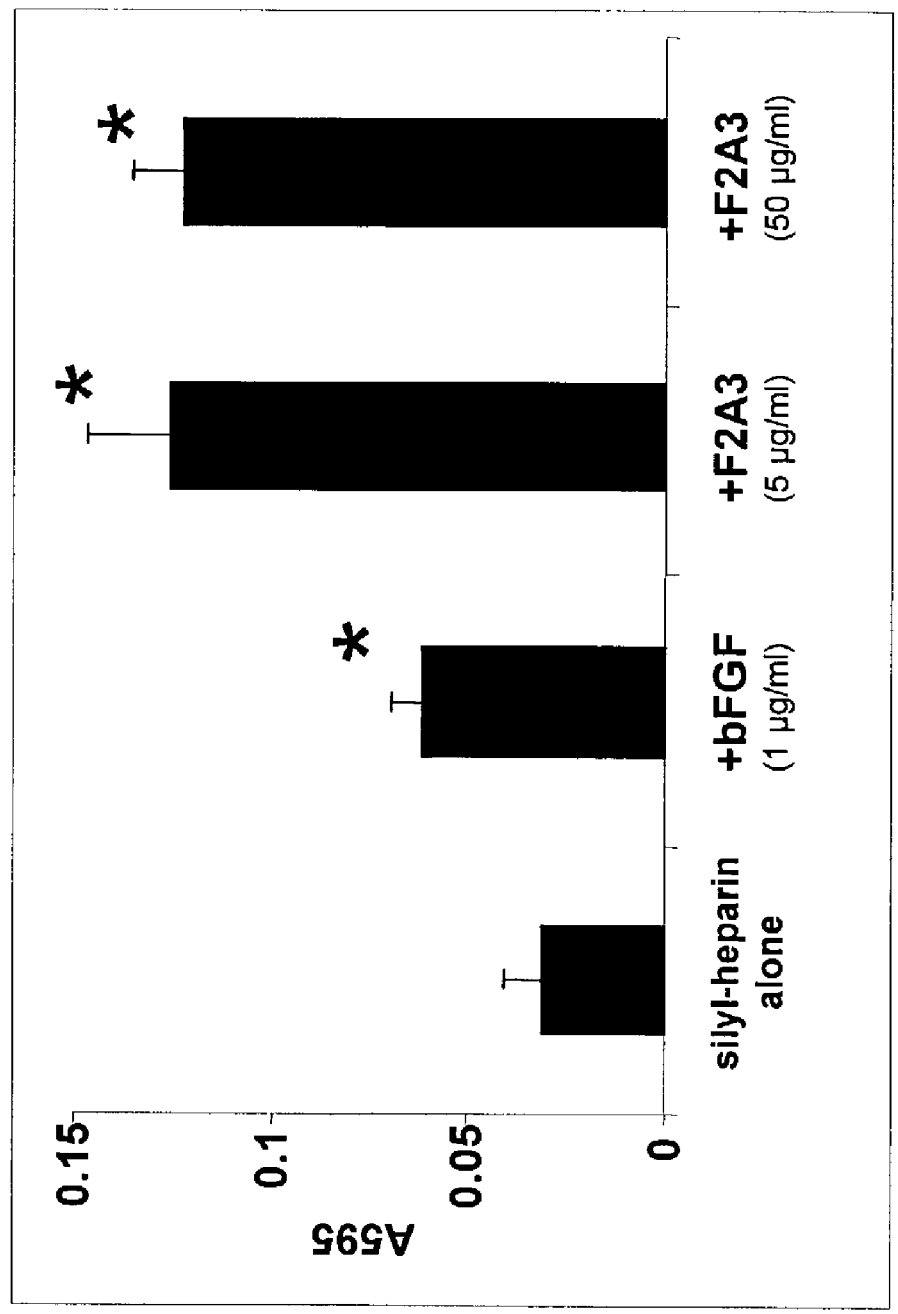
FIG. 7: F2A3 and F2A4 mimic bFGF for cell attachment in vitro. Panel A: Attachment after two hours of CH310T1/2 murine fibroblasts to polystyrene coated with silyl-heparin alone or with silyl-heparin plus bFGF or F2A3. (*) indicates p less than 0.05. Panel B: Micrographs of bovine aortic endothelial cells (BAEC) grown on polycaprolactone with (left panel) or without (right panel) a coating of F2A3.
Figure 7B:
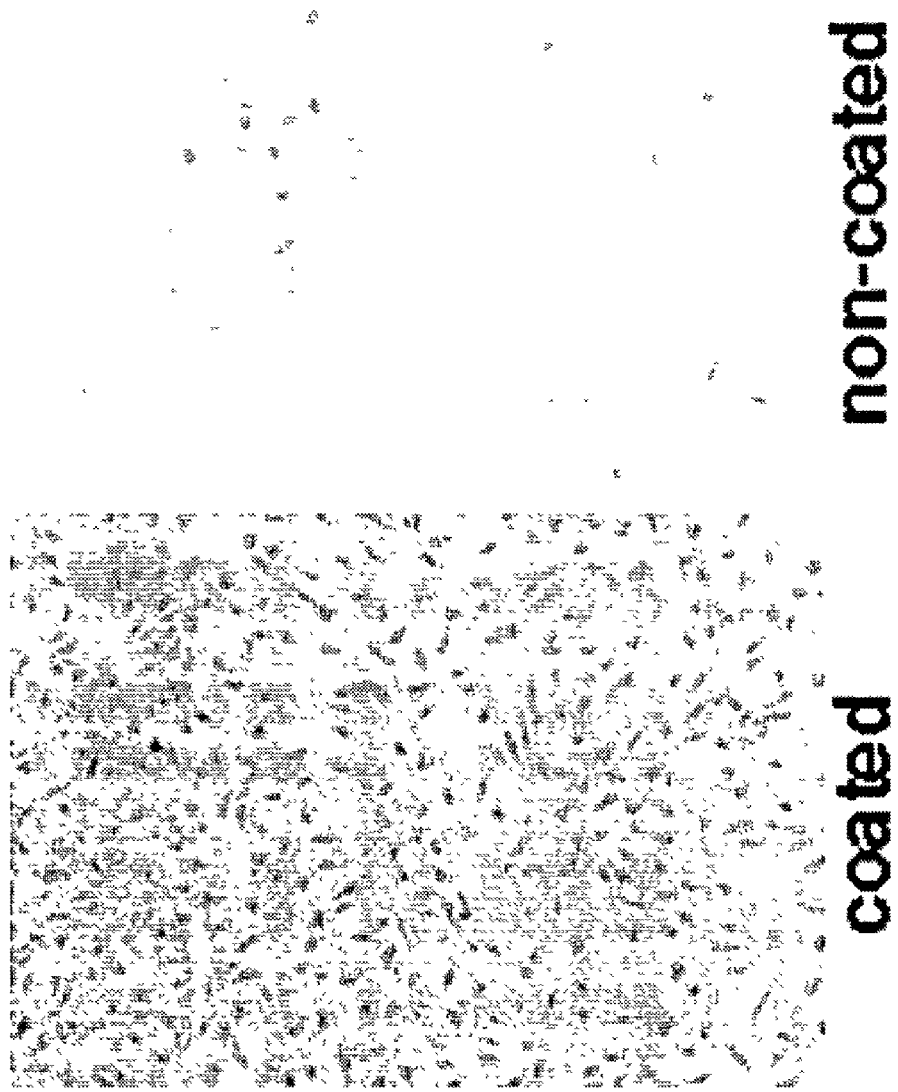

FIGS. 7A and 7B show enhancement of attachment in vitro by F2A3. Attachment of C3H10T1/2 murine fibroblasts to the wells of a polystyrene 96-well tissue culture plate coated with silyl-heparin alone or with silyl-heparin plus bFGF (FGF-2) or silyl-heparin plus F2A3 at the indicated concentrations was measured by absorbance at 595 nm after 2 hours (FIG. 7A).

The panels in FIG. 7B are micrographs of bovine aortic endothelial cells (BEACs) grown on polycaprolactone with (left panel), or without (right panel) a coating of F2A3. Cells were stained with crystal violet and photographed at 100× magnification. Note the relatively high cell density of attached cells on the F2A3 coated specimen.

Example 8

Figure 8:
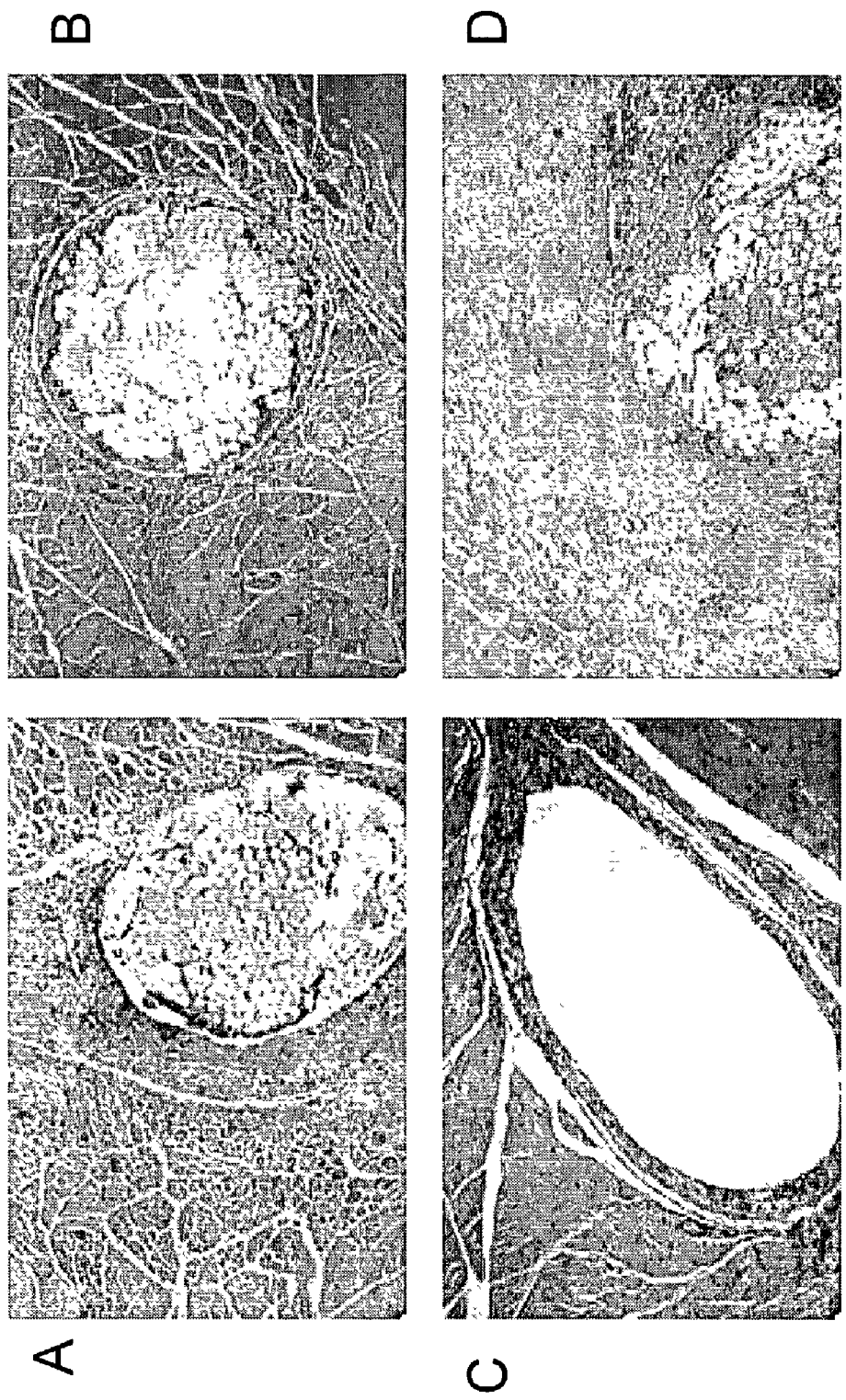
FIG. 8: Photomicrographs of coated polylactide sutures in rat muscle at 2 weeks. Panel A: No coating. B: Silyl heparin coated. C: F2A3 coated. D: Coated with silyl heparin plus F2A3.

FIG. 8 shows the promotion of wound healing by locoregional delivery of F2A3 on biodegradable sutures. Increased granulation and angiogenesis were observed when bioabsorbable Vicryl® polyglycolide/lactide suture (Ethicon Johnson & Johnson, Somerville, N.J., USA) coated to saturation with a combination silyl-heparin+ F2A3 was passed through rat thigh muscle and observed two weeks later in H&E stained histological sections. Panel A demonstrates the morphology after 2 weeks of rat muscle tissue wherein an uncoated suture was introduced. A moderate amount of granulation was found. Panel B, silyl-heparin coated suture. Panel C, F2A3 coated suture. Low to moderate granulation was found. Panel D illustrates the morphology of sutures coated with silyl-heparin+ F2A3. The braided PGLA fibers are evident in cross section, surrounded by a ring of granulation tissue of varying thickness, within a field of striated muscle tissue. Both silyl-heparin alone and F2A3 alone coatings reduced cellularity, compared to control (panels B and C). But the combination of silyl-heparin+ F2A3 caused marked fibroblast proliferation surrounding and infiltrating the braided suture, and increased endothelial cells within the granulation tissue.

Example 9

Figure 9:
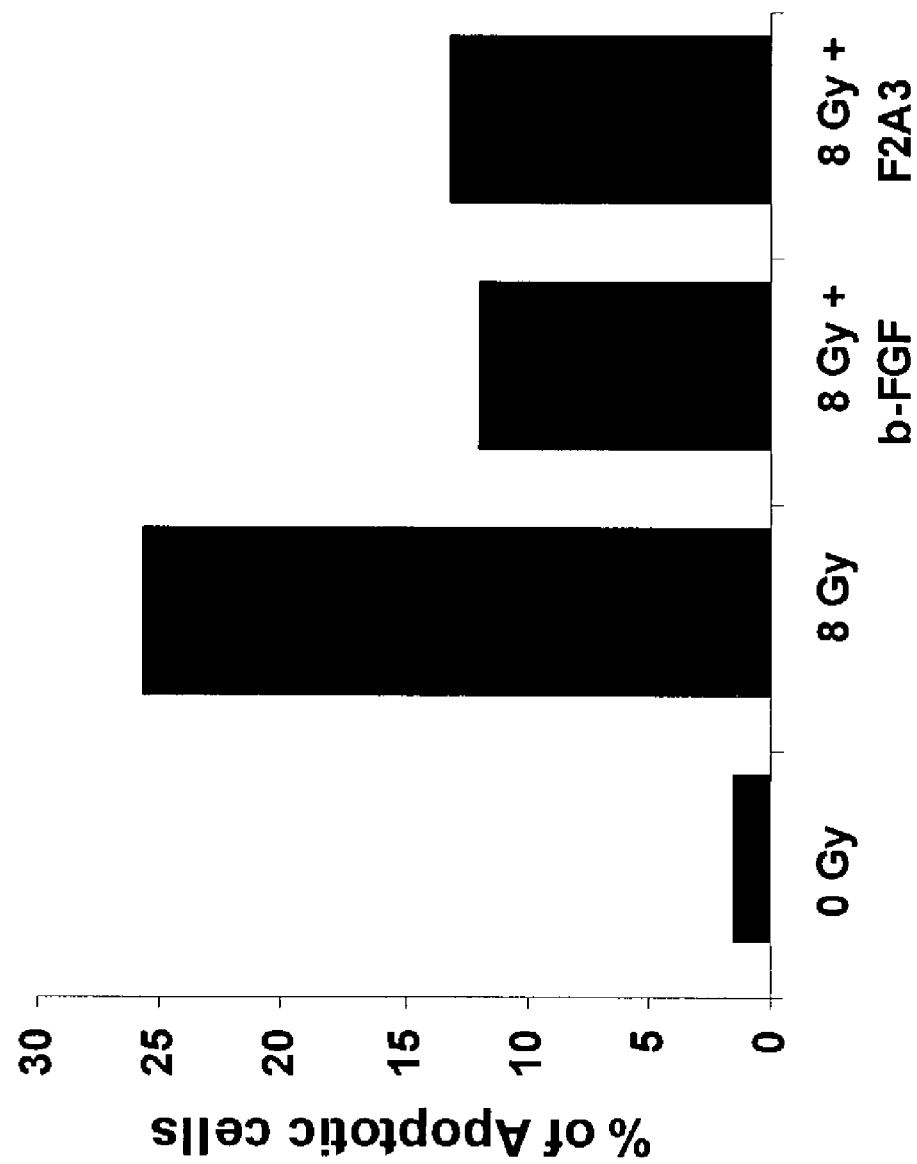
FIG. 9: Radiation protection in endothelial cell cultures. Apoptosis induced by 8 Gy x-ray irradiation is reduced by 50 ng/ml bFGF or F2A3.

FIG. 9 shows the results of a radiation protection experiment in which endothelial cells in culture were irradiated and the percent apoptotic cells measured after treatment with bFGF or F2A3 as compared to untreated controls. Apoptosis was induced by 8 Gy x-ray irradiation and treatment was with 50 ng/ml bFGF or F2A3.

Example 10

Figure 10:
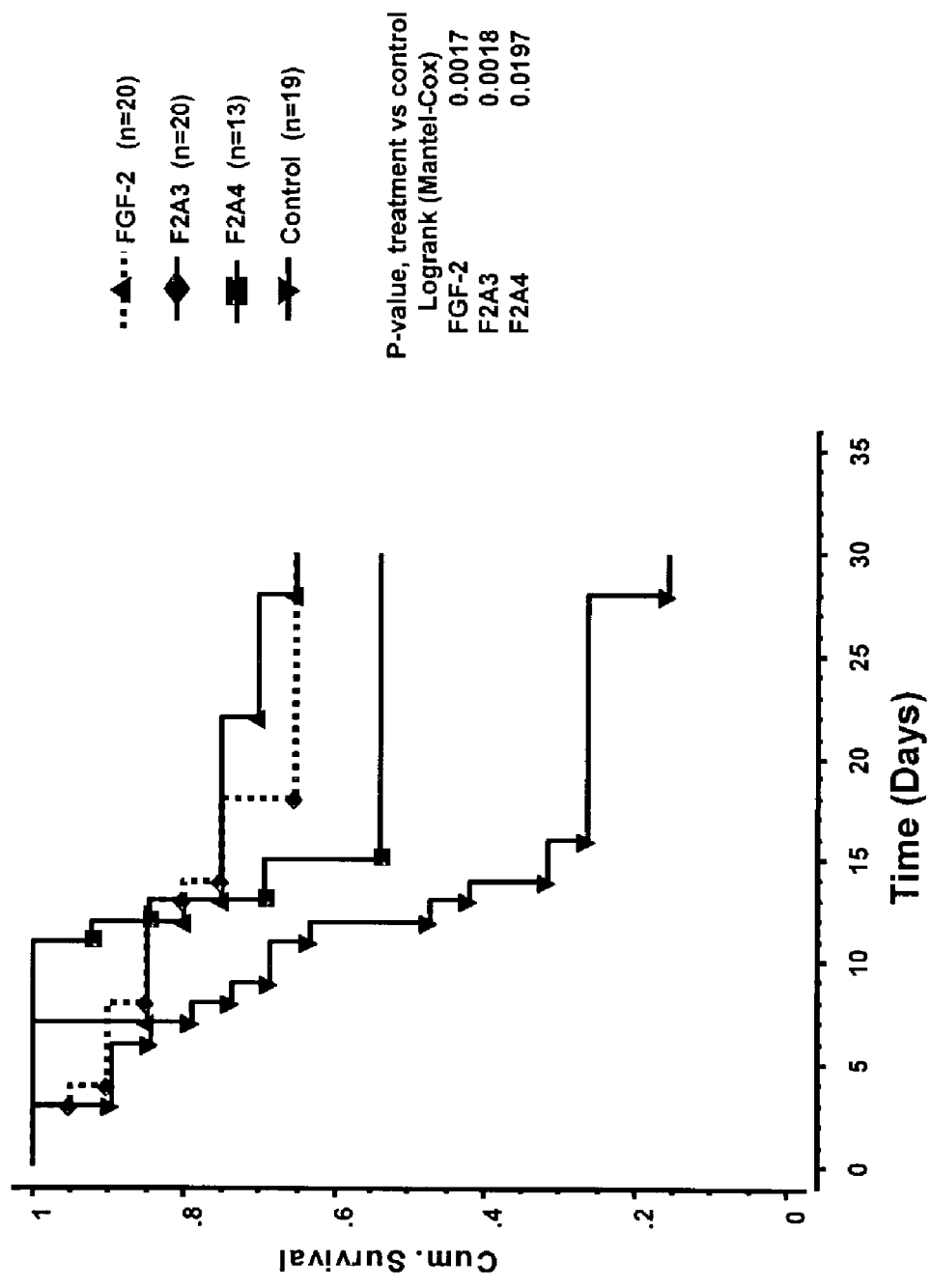
FIG. 10: Radioprotection from G.I. syndrome in vivo.

FIG. 10 shows in vivo radioprotection from gastrointestinal syndrome death by F2A3 and F2A4 compared to bFGF (FGF-2) in the model mouse model developed by Ding & Okunieff (Okunieff et al., Br. J. Cancer. Suppl., 27:S105–8, 1996). Immediately prior to whole body irradiation, adult C57BLxDBA mice were anesthetized by i.p. xylazine/ketamine injection. Subjects were administered by i.v. retro-orbital injection, either 15 µg/mouse of FGF-2 (R&D Systems, Minneapolis, Minn., USA), 5 µg/mouse of F2A3, 5 µg/mouse F2A4, or control vehicle solution (100 µl of 0.2% gelatin in 0.9% NaCl), and then subjected to 14 Gy gamma-irradiation by a $^{137}$Cs source (dose rate 0.93 Gy/min). Animals were monitored twice daily for 30 days, and statistical analysis of survival data was done by the method of Kaplan-Meier.

```
                        SEQUENCE LISTING

<160> NUMBER OF SEQ ID NOS: 4

<210> SEQ ID NO 1
<211> LENGTH: 6
<212> TYPE: PRT
<213> ORGANISM: Artificial
<220> FEATURE:
<223> OTHER INFORMATION: Heparin-binding motif
<220> FEATURE:
<221> NAME/KEY: misc_feature
<222> LOCATION: (1)..(3)
<223> OTHER INFORMATION: LYS or ARG
<220> FEATURE:
<221> NAME/KEY: misc_feature
<222> LOCATION: (4)..(5)
<223> OTHER INFORMATION: any amino acid
<220> FEATURE:
<221> NAME/KEY: misc_feature
<222> LOCATION: (6)..(6)
<223> OTHER INFORMATION: LYS or ARG

<400> SEQUENCE: 1

Xaa Xaa Xaa Xaa Xaa Xaa
1               5

<210> SEQ ID NO 2
<211> LENGTH: 10
<212> TYPE: PRT
<213> ORGANISM: Artificial
<220> FEATURE:
<223> OTHER INFORMATION: Heparin-binding domain of Z region

<400> SEQUENCE: 2

Arg Lys Arg Lys Leu Glu Arg Ala Ile Arg
1               5                   10

<210> SEQ ID NO 3
```

-continued

```
<211> LENGTH: 15
<212> TYPE: PRT
<213> ORGANISM: Artificial
<220> FEATURE:
<223> OTHER INFORMATION: Synthetic FGF analog of FGF-2 of F region

<400> SEQUENCE: 3

Tyr Arg Ser Arg Lys Tyr Ser Ser Trp Tyr Val Ala Leu Lys Arg
1               5                   10                  15

<210> SEQ ID NO 4
<211> LENGTH: 28
<212> TYPE: PRT
<213> ORGANISM: Artificial
<220> FEATURE:
<223> OTHER INFORMATION: Synthetic FGF analog of F region

<400> SEQUENCE: 4

Asn Arg Phe His Ser Trp Asp Cys Ile Lys Thr Trp Ala Ser Asp Thr
1               5                   10                  15

Phe Val Leu Val Cys Tyr Asp Asp Gly Ser Glu Ala
            20                  25
```

The invention claimed is:

1. A synthetic heparin-binding growth factor (HBGF) analog comprising a molecule having the formula (I):

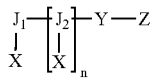

wherein each X represents YRSRKYSSWYVALKR (SEQ ID NO:3), and n is 1;

$J_1$ represents an amino acid;

$J_2$ represents a-diamino acid;

Y represents a linker that (i) is sufficiently hydrophobic to bind non-covalently to a polystyrene or polycaprolactone surface, (ii) comprises a chain of a minimum of about three and a maximum of about 17 residues, (iii) is not found in the natural ligand of the heparin-binding growth factor receptor (HBGFR), and (iv) is covalently bonded to $J_2$ and Z; and Z represents a peptide that comprises a heparin binding domain, comprising RKRKLERAIR (SEQ ID NO:2) and wherein the peptide analog has an avidity for heparin such that the synthetic heparin-binding growth factor analog binds heparin in 0.48M NaCl, but is eluted by 1M NaCl.

2. A synthetic heparin-binding growth factor analog according to claim 1, consisting of a molecule of formula (I).

3. A synthetic heparin-binding growth factor analog according to claim 1, wherein binding of the synthetic heparin-binding growth factor analog to the heparin-binding growth factor receptor initiates a signal by the heparin-binding growth factor receptor.

4. A synthetic heparin-binding growth factor analog according to claim 1, wherein binding of the synthetic peptide to the heparin-binding growth factor receptor blocks signaling by the heparin-binding growth factor receptor.

5. A synthetic heparin-binding growth factor analog according to claim 1, wherein $J_1$ and/or $J_2$ is an $\alpha$-amino acid.

6. A synthetic heparin-binding growth factor analog according to claim 1, wherein $J_2$ is lysine.

7. A synthetic heparin-binding growth factor (HBGF) analog comprising a molecule having the formula (I):

wherein each X represents YRSRKYSSWYVALKR (SEQ ID NO:3), and n is 1;

$J_1$ represents lysine;

$J_2$ represents lysine;

Y represents a linker covalently bonded to $J_2$ and Z; and

Z represents a heparin binding sequence comprising RKRKLERAIR (SEQ ID NO:2).

8. The analog of claim 7 wherein Y is Hex-Hex-Hex (aminohexanoic acid tripeptide).

* * * * *

UNITED STATES PATENT AND TRADEMARK OFFICE
CERTIFICATE OF CORRECTION

PATENT NO. : 7,166,574 B2
APPLICATION NO. : 10/224268
DATED : January 23, 2007
INVENTOR(S) : Louis A. Peña et al.

It is certified that error appears in the above-identified patent and that said Letters Patent is hereby corrected as shown below:

2. In Claim 7, formula (I) is replaced as shown:

$$\left[ J_1 - \left[ J_2 - Y - Z \atop | \right]_n \right]$$
$$\phantom{\left[ J_1 -}\, X \ \ X$$

Signed and Sealed this

Fourth Day of December, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,166,574 B2 | Page 1 of 1 |
| APPLICATION NO. | : 10/224268 | |
| DATED | : January 23, 2007 | |
| INVENTOR(S) | : Louis A. Pena et al. | |

It is certified that error appears in the above-identified patent and that said Letters Patent is hereby corrected as shown below:

Col. 17, lines 9 and 10, is replaced as shown:

RKRKLERIAR (SEQ ID NO:2)

Col. 21, line 49, is replaced as shown:

RKRKLERIAR (SEQ ID NO:2)

Col. 22, line 54, is replaced as shown:

RKRKLERIAR (SEQ ID NO:2)

Sequence Listing, SEQ ID NO 2, below Cols. 19 and 20, is replaced as shown:

<400> SEQUENCE: 2

Arg Lys Arg Lys Leu Glu Arg Ile Ala Arg
1                                       10

Signed and Sealed this

Twentieth Day of January, 2009

JON W. DUDAS
*Director of the United States Patent and Trademark Office*